(12) United States Patent
Vafi

(10) Patent No.: US 11,813,186 B2
(45) Date of Patent: Nov. 14, 2023

(54) WEARABLE SITTING-POSTURE AID

(71) Applicant: noonee AG, Hedingen (CH)

(72) Inventor: Daniel Vafi, Zurich (CH)

(73) Assignee: noonee AG, Hedingen (CH)

( * ) Notice: Subject to any disclaimer, the term of this patent is extended or adjusted under 35 U.S.C. 154(b) by 475 days.

(21) Appl. No.: 16/969,709

(22) PCT Filed: Feb. 14, 2019

(86) PCT No.: PCT/EP2019/053621
§ 371 (c)(1),
(2) Date: Aug. 13, 2020

(87) PCT Pub. No.: WO2019/158623
PCT Pub. Date: Aug. 22, 2019

(65) Prior Publication Data
US 2021/0000630 A1    Jan. 7, 2021

(30) Foreign Application Priority Data
Feb. 14, 2018    (DE) ................ 10 2018 103 302.8

(51) Int. Cl.
*A61F 5/01*    (2006.01)
*A47C 9/10*    (2006.01)
(Continued)

(52) U.S. Cl.
CPC ............ *A61F 5/0125* (2013.01); *A47C 9/025* (2013.01); *A47C 9/10* (2013.01); *A61G 5/14* (2013.01)

(58) Field of Classification Search
CPC .. A61G 5/14; A47C 9/10; A47C 9/025; A61F 5/0125; A61F 5/0127
See application file for complete search history.

(56) References Cited

U.S. PATENT DOCUMENTS 4,138,156 A    2/1979  Bonner
4,641,882 A    2/1987  Young
(Continued)

FOREIGN PATENT DOCUMENTS

CN    106377394 A      2/2017
CN    106859122 A  *  6/2017
(Continued)

OTHER PUBLICATIONS

Japanese Office Action dated Oct. 25, 2022 in corresponding Japanese Patent Application No. JP 2020-543271 (and English summary).

(Continued)

*Primary Examiner* — Milton Nelson, Jr.
(74) *Attorney, Agent, or Firm* — POSZ LAW GROUP, PLC

(57) ABSTRACT

A wearable sitting-posture assisting device includes at least one leg unit that defines at least one longitudinal leg axis, and includes at least one foot unit that is configured for a connection of a shoe and/or a foot of a person, wherein the foot unit includes at least one shoe adapter and at least one shoe connector, which are couplable with one another at least transversely to the at least one at least one longitudinal leg axis, wherein the wearable sitting-posture assisting device includes a quick coupling which is configured for a tool-less coupling of the shoe adapter and the shoe connector with each other, wherein the quick coupling includes at least one latch element that is configured at least partially to create a coupling of the shoe adapter with the shoe connector.

11 Claims, 10 Drawing Sheets

Figure 1:
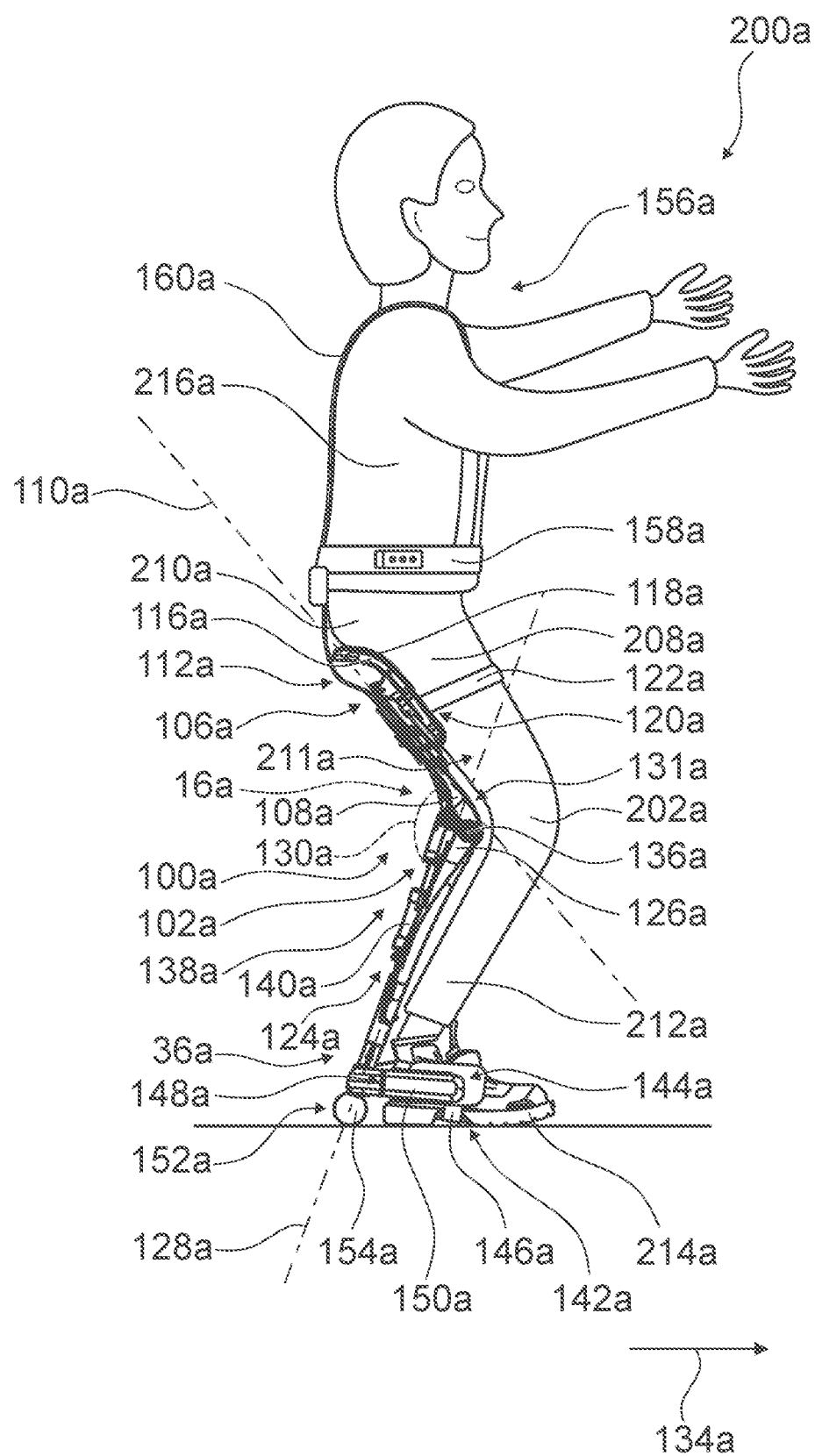

(51) Int. Cl.
*A61G 5/14* (2006.01)
*A47C 9/02* (2006.01)

(56) References Cited

U.S. PATENT DOCUMENTS

| | | | | |
|---|---|---|---|---|
| 6,024,713 | A | * | 2/2000 | Barney ............... A61F 5/0125 602/26 |
| 2014/0148738 | A1 | | 5/2014 | Nagasaka et al. |

FOREIGN PATENT DOCUMENTS

| | | | |
|---|---|---|---|
| DE | 102013019079 A1 | | 5/2015 |
| EP | 3158894 A1 | | 4/2017 |
| EP | 3318240 A1 | | 5/2018 |
| FR | 3048596 A1 | * | 9/2017 |
| JP | 3-243488 A | | 10/1991 |
| JP | 2011-125546 A | | 6/2011 |
| JP | 2014-104185 A | | 6/2014 |
| WO | WO-2015017576 A1 | * | 2/2015 ........... A61K 39/395 |
| WO | 2015153633 A2 | | 10/2015 |
| WO | 2016/210446 A1 | | 12/2016 |
| WO | 2017191173 A1 | | 11/2017 |

OTHER PUBLICATIONS

German Search Report dated on Dec. 13, 2018 issued in corresponding DE patent application No. 10 2018 103 302.8 (and English Translation).
International Search Report dated on Jul. 22, 2019 issued in corresponding international application No. PCT/EP2019/053621.
International Preliminary Report on Patentability dated on Aug. 18, 2020 issued in corresponding international application No. PCT/EP2019/053621.

* cited by examiner

WEARABLE SITTING-POSTURE AID

CROSS REFERENCE TO RELATED APPLICATIONS

This application is a U.S. national stage application of PCT/EP2019/053621 filed on Feb. 14, 2019, which is based on German Patent Application No. 10 2018 103 302.8 filed on Feb. 14, 2018, the contents of which are incorporated herein by reference.

STATE OF THE ART

The invention relates to a wearable sitting-posture assisting device, to a foot unit and to a method for an operation of the wearable sitting-posture assisting device.

The objective of the invention is in particular to provide a generic device and/or a method for an operation of the device with improved characteristics regarding comfort, ergonomics and/or physiology.

Advantages of the Invention

The invention is based on a wearable sitting-posture assisting device with at least one leg unit that defines at least one longitudinal leg axis, in particular an upper longitudinal leg axis and/or a lower longitudinal leg axis, and with at least one foot unit that is configured for a connection of a shoe and/or a foot of a person, wherein the foot unit comprises at least one shoe adapter and at least one shoe connector, which are couplable with one another at least transversely to the longitudinal leg axis, in particular the upper longitudinal leg axis and/or the lower longitudinal leg axis.

It is proposed that the wearable sitting-posture assisting device comprises a quick coupling which is configured for a tool-less coupling of the shoe adapter and the shoe connector with each other, wherein the quick coupling comprises at least one latch element that is configured at least partially to create a coupling of the shoe adapter with the shoe connector. This allows improving comfort, in particular a wearing comfort, and/or ergonomics. It is in particular possible to increase the wearing comfort as a quick coupling and/or uncoupling of a user's feet, in particular both in a sitting posture and in a standing posture as well as when walking, is simplified by the foot unit. In particular, the wearing comfort in a sitting posture and/or standing posture can be improved as it is possible for a user's feet to be coupled and/or uncoupled in individual positions, i.e. in particular in the sitting posture, in the standing posture and/or when walking. Preferably, moreover the wearing comfort when walking can be improved as a quick uncoupling and/or coupling-in is achievable when changing between walking and sitting posture. Furthermore safety, in particular operational safety and/or usage safety, are/is improvable. It is in particular possible to avoid joints and/or body parts being loaded and/or being blocked by the wearable sitting-posture assisting device in an undesired fashion as body parts can be quickly uncoupled from the wearable sitting-posture assisting device in case of an overload on said body parts. The quick coupling advantageously allows further improving comfort, in particular a wearing comfort, as further tools for coupling may be done without. It is in particular possible to improve safety as a coupling and/or decoupling can be effected without tools in emergency situations as well.

By a "quick coupling" is in particular a preferably mechanical and/or magnetic unit to be understood which is configured for a tool-less, non-destructive and/or repeatable coupling of two structural components with each other, preferably in a one-handed, one-legged and/or one-footed manner, and very particularly advantageously with a single movement of a hand, a foot and/or a leg of a person. For example, a quick coupling may implement a hook-and-loop fastener, a magnetic lock, a clip and/or latch closure, a twist lock and/or a bayonet lock, or the like. Preferably the quick coupling comprises a combination of a magnetic lock and a latch closure. In particular for coupling purposes, the quick coupling comprises at least one quick coupling element and at least one further quick coupling element that is embodied correspondingly to the quick coupling element. The quick coupling element is in particular arranged on the shoe adapter. The further quick coupling element is in particular arranged on the shoe connector. In particular, the quick coupling may be realized at least partly integrally with the foot unit, in particular with the shoe adapter and/or with the shoe connector. Preferentially the quick coupling element could be embodied at least partly integrally with the shoe adapter. In particular, the further quick coupling element could be embodied at least partly integrally with the shoe connector.

By a "latch element" is in particular a preferably elastic element to be understood which is configured to create at least one latch connection, for example by a force-fit and/or form-fit connection. In particular, the further quick coupling element comprises the latch element. Alternatively the quick coupling element could be embodied integrally with the latch element. The latch element has a protrusion that is, for example, cone-shaped. Furthermore the quick coupling comprises at least one further latch element, which is preferably embodied correspondingly to the latch element. The further quick coupling element in particular comprises the further latch element. Alternatively the further quick coupling element could be embodied integrally with the further latch element. In particular for a coupling, the further latch element is configured to engage behind the latch element, in particular the protrusion.

In a further aspect of the invention it is proposed that the wearable sitting-posture assisting device comprises at least one bearing unit supporting at least a portion of the foot unit such that it is translationally movable at least transversely to the at least one longitudinal leg axis, in particular the upper longitudinal leg axis and/or the lower longitudinal leg axis. This allows improving comfort, in particular a wearing comfort, ergonomics and/or physiology. It is in particular possible to increase the wearing comfort as a user's freedom of movement is augmented by means of the bearing unit, namely in particular both in a sitting posture and in a standing posture as well as when walking. The wearing comfort can in particular be improved in a sitting posture and/or standing posture as the bearing unit permits an individual positioning of the foot unit and thus of a user's feet. Preferentially it is moreover possible to improve the wearing comfort when walking as the bearing unit permits a stretching and contraction of the feet relative to the leg, which is necessary for walking. As a result, it is in particular possible for a physiology of the wearable sitting-posture assisting device to be improved when walking. Moreover in particular safety, in particular operational safety and/or usage safety, is improvable. In particular by the bearing unit it is avoidable that movement processes, joints and/or body parts are blocked and/or overloaded in an undesired fashion.

By a "wearable sitting-posture assisting device" is here in particular a device to be understood which is configured to at least partially, preferably at least to a large extent and particularly preferably completely receive a weight force of a person who is in a sitting posture or in a partial sitting posture, and to transfer the weight force at least partly, preferably at least to a large extent and particularly preferably completely to a ground. "Configured" is in particular to mean specifically programmed, designed and/or equipped. By an object being configured for a certain function is in particular to be understood that the object fulfills and/or executes said certain function in at least one application state and/or operation state. The term "at least to a large extent" is here in particular to mean at least by 55%, preferably at least by 65%, preferentially at least by 75%, especially preferentially at least by 85% and very particularly preferably at least by 95%. The wearable sitting-posture assisting device in particular permits the person by whom it is worn to walk about according to the person's wishes and requirements, to stand and/or to sit down on the wearable sitting-posture assisting device as well as to get up after sitting or partially sitting on the wearable sitting-posture assisting device. In particular, an angle between the person's thigh and the person's shank is in the sitting posture maximally 130°, preferably maximally 120° and particularly preferably maximally 110°, and/or in particular at least 60°, preferably at least 70° and particularly preferably at least 80°. Preferentially in the sitting posture the angle between the person's thigh and the person's shank is at least substantially 90°. "At least substantially" is in particular to mean a consideration of a deviation from a given value by maximally 15%, preferably maximally 10%, preferentially maximally 5% and very especially preferentially maximally 1%. In particular, in the partial sitting posture an angle between the person's thigh and the person's shank is maximally 170°, preferably maximally 160° and particularly preferably maximally 150°, and/or in particular at least 100°, preferably at least 110° and particularly preferably at least 120°. Preferentially in the partial sitting posture the angle between the person's thigh and the person's shank is at least substantially 130°. By a "partial sitting posture" is in particular a posture to be understood in which a person leans forward while at the same time partially bending his knees. In particular, a person wearing the wearable sitting-posture assisting device may sit and/or partially sit and/or sit down on the wearable sitting-posture assisting device, wherein the wearable sitting-posture assisting device at least partly, preferably at least to a large extent and particularly preferably completely acts against the weight force and/or wherein the person acts only against a fraction of his weight force by muscle force. A "fraction" is in particular to mean a portion of an entirety amounting to maximally 15%, preferably maximally 10% and particularly preferably no more than 5% of the entirety. The wearable sitting-posture assisting device is in particular configured to be worn by the person while the person is standing and/or while the person is walking. By "an object being worn by a person" is in particular to be understood that the object is worn by a person on his body and/or is put onto his body, as is the case, for example, with a piece of clothing and/or work equipment. Advantageously the wearable sitting-posture assisting device is configured to support different sitting postures and/or partial sitting postures, which are in particular defined by different sitting angles.

The wearable sitting-posture assisting device in particular defines a sitting direction. Preferably the person looks in the sitting direction and/or faces towards the sitting direction when sitting or partially sitting on the wearable sitting-posture assisting device and facing forward. In particular, the sitting direction is oriented parallel to a ground which the person is sitting above and/or which the person is standing and/or walking on while wearing the wearable sitting-posture assisting device. The wearable sitting-posture assisting device in particular defines a walking direction. Preferentially the person faces in the walking direction when walking and/or standing with the wearable sitting-posture assisting device and facing forward. In particular, the walking direction is oriented parallel to a ground which the person is sitting above and/or which the person is standing and/or walking on while wearing the wearable sitting-posture assisting device. In particular, the wearable sitting-posture assisting device is designed only for receiving and transferring the weight force. Preferentially the wearable sitting-posture assisting device is not designed to generate a controllable force configured for supporting a person while walking, standing and/or lifting loads.

The leg unit in particular comprises at least one, preferably an upper, leg part and/or at least one, preferably a lower, leg part. The upper leg part is in particular allocated to a a thigh of a person wearing the sitting-posture assisting device and/or is fixated on the thigh. A main extension of the lower leg part defines a lower longitudinal leg axis. The lower leg part is in particular allocated to a shank of a person wearing the sitting-posture assisting device and/or is fixated on the shank. In particular, the upper leg part and the lower leg part are connected to one another in such a way that they are movable relative to one another. A main extension of the upper leg part defines an upper longitudinal leg axis. The leg unit advantageously comprises at least one, preferably one single, knee joint that connects the upper leg part and the lower leg part.

The foot unit is in particular connected with the leg unit, in particular the lower leg part. The shoe connector of the foot unit is in particular configured for a coupling and/or connection of a shoe and/or foot with the leg unit. By "two structural components being couplable" is in particular to be understood that these are connectable with each other and are, in particular repetitively, preferably non-destructively separable from each other. A coupling of two structural components may be generated, for example, by a force-fit and/or form-fit connection. A "force-fit and/or form-fit connection" is herein in particular to mean a releasable connection, wherein a holding force between the two structural components is preferably transferred via a geometric engagement of the structural components into each other and/or by a friction force between the structural components. In a coupling of two structural components in particular a substance-to-substance bond between the structural components is precluded. A "substance-to-substance bond" is in particular to mean that the mass particles are held together by atomic or molecular forces like, for example, in the case of soldering, welding, gluing and/or vulcanization. In particular, the shoe adapter and the shoe connector are couplable with each other along a coupling direction that extends transversely to the longitudinal leg axis, in particular the upper longitudinal leg axis and/or the lower longitudinal leg axis, by way of the shoe adapter and the shoe connector being guided along the coupling direction one upon the other one and/or one within the other one. In particular, the coupling direction is at least substantially orthogonal to an expansion direction and/or contraction direction of the bearing unit.

The shoe connector is in particular configured to be worn on a person's shoe and/or foot. The shoe connector advantageously comprises at least one shoe strap. In particular, the shoe connector comprises at least one upper strap, which advantageously extends transversely across an instep of the foot or shoe which the foot unit is connected to. Preferentially the shoe connector comprises at least one lower strap, which advantageously extends transversely across a sole of the foot or shoe which is connected by means of the foot unit. "Transversely" is in particular to mean an arrangement different than an at least substantially parallel arrangement. Preferentially a transverse arrangement is to mean an at least substantially orthogonal arrangement. In particular, in a wearing-the-shoe-connection state the person wears the shoe connector on the shoe and/or on the foot. The shoe connector is in the wearing-the-shoe-connection state preferably attached to the person's shoe and/or foot. In particular, in the normal wearing state the shoe connector is in a wearing-the-shoe-connection state. The foot unit advantageously comprises at least one shoe adapter. The shoe adapter is preferably implemented to be couplable with the shoe connector. The shoe connector is hence connectable to the leg unit via the shoe adapter. The component of the foot unit that is supported in a translationally movable manner is in particular at least the shoe adapter and/or the shoe connector of the foot unit.

Advantageously the foot unit comprises at least one foot unit support. The foot unit support is preferably embodied as a bracket. It is conceivable that the foot unit support is implemented at least partly integrally or integrally with the lower leg part, in particular with the lower leg support. In particular, the bearing unit is arranged on the foot unit support or is implemented at least partly integrally with the foot unit support. The bearing unit of the foot unit is a unit configured to form a bearing. In particular, the bearing unit comprises at least one bearing element and at least one further bearing element, which are configured at least to form the bearing and preferably mutually guide each other. It is conceivable that the bearing unit is embodied as a slide bearing, in particular with the bearing element and the further bearing element being realized in such a way that they correspond to each other and contact each other to form a slide bearing. In particular, the bearing element comprises at least one guide element and the further bearing element comprises a corresponding guide element, the guide elements preferably engaging around each other at least partially. The guide elements are in particular implemented as corresponding guide rails. Alternatively the bearing unit could be embodied as a roller bearing, wherein the bearing unit preferably, in addition to forming the bearing, comprises at least one, preferentially a plurality of roller elements which are arranged between the bearing element and the further bearing element, in particular their respective guide elements, for the purpose of supporting these in such a way that they roll on each other. Such a roller element could for example be embodied as a sphere, a roll or the like. In particular, the bearing element is at least displaceable relative to the further bearing element. The bearing element and the further bearing element are translationally movable relative to one another. By "translationally" is in particular a type of a movement of an object to be understood in which all points of the object undergo the same displacement, wherein preferably velocities and accelerations of all points are identical. In particular, a translational movement differs from a rotational movement. In particular, at least the shoe adapter and/or the shoe connector are/is arranged on the bearing unit and/or are/is connected therewith. Alternatively or additionally it is conceivable that the shoe adapter and/or the shoe connector are preferably respectively implemented at least partly integrally with the bearing unit. For example, the bearing element could be implemented at least partly integrally with the shoe adapter. Furthermore, for example, the further bearing element could be implemented at least partly integrally with the shoe connector.

The leg unit furthermore in particular comprises at least one ground contact unit. In particular the ground contact unit comprises at least one ground contact element. The ground contact element preferably comprises at least one ground contact surface, which is advantageously configured to contact a ground when the person is sitting or partially sitting on the wearable sitting-posture assisting device. The ground contact surface is advantageously bent and/or curved, in particular convexly bent and/or convexly curved. Preferentially at least a portion of the ground contact element or the entire ground contact element is ellipsoid-shaped and/or rotational-ellipsoid-shaped and/or sphere-shaped. The ground contact element is in particular implemented at least partly, preferably at least to a large extent, advantageously completely of rubber. Preferably a weight force of the person is transferred from the seat unit to the upper leg support and/or from the upper leg support to the knee joint and/or from the knee joint to the lower leg support and/or from the lower leg support to the ground contact element and/or from the ground contact element to the ground. In particular, the weight force of the person is additionally transferred to the ground via the person's foot or shoe. When the person is sitting or partially sitting on the wearable sitting-posture assisting device, in addition to the ground contact element the person's foot and/or shoe are/is in contact with the ground. Preferentially the ground contact element is arranged contact-free relative to the ground when the person is walking or standing while wearing the wearable sitting-posture assisting device. The ground contact unit is in particular connected with the lower leg part and/or with the foot unit. It is conceivable that the ground contact unit is realized at least partly integrally with the lower leg part and/or at least partly integrally with the foot unit. It is also conceivable that the foot unit is realized at least partly integrally with the lower leg part. By "connected and/or realized at least partly integrally" is in particular to be understood, in this context, that an object comprises at least one structural component that is integrally connected with at least one further structural component of the object. "Integrally" is in particular to mean connected at least by substance-to-substance bond, for example by a welding process, a gluing process, an injection-molding process and/or another process that is deemed expedient by someone skilled in the art. Advantageously integrally is also to mean in one piece. "In one piece" is in particular to mean formed in one piece, for example by a production from one cast and/or by a production in a one- or multi-component injection-molding process and advantageously from a single blank.

The wearable sitting-posture assisting device in particular comprises at least one upper body wearing unit. In particular, the leg unit is connected with the upper body wearing unit, namely preferably by at least one connection strap. Preferentially the person wearing the wearable sitting-posture assisting device wears the upper body wearing unit on his upper body. Advantageously the upper body wearing unit is embodied as a belt and/or as suspenders and/or as buckles.

The wearable sitting-posture assisting device in particular comprises at least one additional leg unit. The wearable sitting-posture assisting device preferentially comprises at least one, preferably exactly one leg unit for each leg of a person. In particular, the wearable sitting-posture assisting device comprises two, advantageously exactly two leg units. Advantageously the leg unit and the additional leg unit are embodied identically. It is also conceivable that the leg unit and the additional leg unit are embodied mirror-symmetrically to each other. It is conceivable that the leg unit is configured to be worn on a left leg and the additional leg unit is configured to be worn on a right leg, or vice versa. Advantageously the leg unit is configured to be worn either on a left leg or on a right leg. Further advantageously the additional leg unit is configured to be worn on a right leg. Preferentially the additional leg unit is connected with the upper body wearing unit, preferably by means of at least one connection strap. In particular, the person wearing the wearable sitting-posture assisting device wears the leg unit, in particular only the leg unit, on a first leg, e.g. a left leg or a right leg. In particular, the person wearing the wearable sitting-posture assisting device wears the additional leg unit, in particular only the additional leg unit, on a second leg, e.g. a right leg or a left leg. Advantageously the leg unit is arranged on a rear side of the leg which the leg unit is worn on. Further advantageously the additional leg unit is arranged on a rear side of the leg which the additional leg unit is worn on. In particular, the leg units of the wearable sitting-posture assisting device are arranged on rear sides of the person's legs while the person is sitting and/or partially sitting on the wearable sitting-posture assisting device and/or is standing and/or walking with the wearable sitting-posture assisting device.

For a connection with a thigh of the person, the upper leg part preferably comprises at least one thigh connection unit. The thigh connection unit preferentially comprises at least one thigh strap In particular, the upper leg part comprises a seat unit which is configured, in particular if the person is sitting or partly sitting on the wearable sitting-posture assisting device, to provide a sitting surface for the person, preferably for the person's thigh and/or at least for a lower portion of a buttock of the person. Preferably the seat unit has at least one seat element that comprises the sitting surface. Advantageously the seat unit is in contact with the person's thigh when the person is sitting or partly sitting on the wearable sitting-posture assisting device. Preferably the seat unit is arranged on a rear side of the person's thigh when the person is standing or walking with the wearable sitting-posture assisting device.

The upper leg part advantageously comprises at least one upper leg support. Preferentially the seat unit is connected with the upper leg support. Advantageously the thigh connection unit and/or the thigh strap are/is connected with the upper leg support. In particular, the upper leg support is implemented as a frame element. Preferably the upper leg support is implemented as an elongate element. Advantageously the upper leg part has at least one upper longitudinal leg axis, which is oriented at least substantially parallel to a longitudinal axis of the person's thigh. Preferably a main extension direction of the upper leg support is oriented at least substantially parallel to the upper longitudinal leg axis. "At least substantially parallel" is in particular to mean an orientation of a direction relative to a reference direction wherein, in particular viewed in a plane, the direction and the reference direction include an angle of 0°, the angle in particular having a maximum deviation of in particular less than 8°, advantageously less than 5° and especially advantageously less than 2°. In particular, the upper leg support is made at least partly, preferably at least to a large extent, advantageously completely of a synthetic material. It is also conceivable that the upper leg support is made at least partly, preferably at least to a large extent, advantageously completely of a lightweight metal or a lightweight metal alloy, e.g. aluminum and/or titanium and/or beryllium and/or scandium or other suitable metals. It is further conceivable that the upper leg support is made at least partly, preferably at least to a large extent, advantageously completely of a composite material, in particular a fiber composite material and/or a fiber-reinforced synthetic material and/or a carbon-fiber composite material and/or a carbon-fiber-reinforced polymer and/or a fiber-reinforced thermoplastic material. The lower leg part is preferably arranged on a rear side of a shank of the person. In particular, the lower leg part comprises at least one lower leg support. Advantageously the lower leg support is implemented as a frame element. Preferentially the lower leg support is implemented as an elongate element.

Preferably respective orientations of the upper leg part and the lower leg part together define a sitting angle. The sitting angle is preferentially an angle spanned between the upper longitudinal leg axis and the lower longitudinal leg axis, in particular on a respective rear side of the upper leg part and the lower leg part. In particular, in the sitting posture the sitting angle is maximally 130°, preferably maximally 120° and particularly preferably maximally 110°, and/or in particular at least 60°, preferably at least 70° and particularly preferably at least 80°. In particular, the sitting angle is in the sitting posture at least substantially 90°. In particular, in the partial sitting posture the sitting angle is no more than 170°, preferably maximally 160° and advantageously no more than 150°, and/or in particular at least 100°, preferably at least 110° and particularly preferably at least 120°. In particular, the sitting angle is in the partial sitting posture at least substantially 130°. Preferentially the sitting angle corresponds to the angle between the thigh and the shank of the person. In particular, the sitting angle is at least substantially 180° in a standing posture.

In particular, the knee joint connects the lower leg part with the upper leg part in such a way that it is pivotable, in particular pivotable around a knee joint axis. Advantageously the knee joint axis is oriented at least substantially orthogonally to the upper longitudinal leg axis and/or to the lower longitudinal leg axis. Preferentially the knee joint axis is oriented at least substantially orthogonally to the sitting direction. "At least substantially orthogonally" is in particular to mean an orientation of a direction relative to a reference direction wherein, in particular viewed in a plane, the direction and the reference direction include an angle of 90°, the angle in particular having a maximum deviation of in particular less than 8°, advantageously less than 5° and especially advantageously less than 2°. Advantageously the upper leg support and the lower leg support together form at least a portion of the knee joint or the knee joint. Preferably a value of the sitting angle corresponds to a value of a knee joint position of the knee joint.

Preferentially the wearable sitting-posture assisting device comprises at least one blocking unit that is configured for a blocking of the upper leg part in a defined sitting angle relative to the lower leg part and/or to the knee joint, and/or is configured to define a smallest sitting angle. Advantageously the blocking unit is configured to block the knee joint in different sitting angles and/or to define different smallest sitting angles, which are preferably selectable by the person. It is conceivable that the blocking unit is configured to permit increasing the sitting angle in a blocked state. In particular, it permits the person to get up when the blocking unit is in the blocked state. Preferentially the blocking unit is configured to allow the person, after getting up with the blocking unit defining a certain smallest sitting angle, to sit down again with the certain defined smallest sitting angle. Advantageously the blocking unit comprises at least one blocking element, which is configured to block and/or unblock the knee joint and/or to block the sitting angle and/or to define a smallest sitting angle. Preferentially the blocking element is implemented as a spring, in particular a gas compression spring. The blocking element is advantageously connected with the upper leg part, in particular the upper leg support, and with the lower leg part, in particular the lower leg support. The blocking element is preferably configured for a damping of a movement of the upper leg part relative to the lower leg part during sitting down and/or getting up. Advantageously the blocking unit comprises at least one actuation element that is configured for an actuation of the blocking element. Preferentially the actuation element is configured to allow the person a blocking or unblocking of the blocking element. Advantageously the actuation element is a mechanical actuation element. It is also conceivable that the actuation element is an electronical actuation element. Furthermore it is conceivable that the blocking unit comprises at least one control unit that is configured to detect, depending on requirements, following a blocking of the blocking element, a sitting-down state when the person sits down, and/or to detect a getting-up state when the person gets up, and/or to activate the actuation element.

It is also proposed that the leg unit defines at least one leg bending plane, relative to which the bearing unit supports the foot unit in an at least partly at least substantially parallel-translationally movable manner. Advantageously comfort, in particular a wearing comfort, can be improved. It is in particular possible to improve a mobility during locomotion. It is especially advantageously possible to improve a posture of a person in a sitting posture, in particular by providing the person with additional freedom of movement for a positioning of his feet relative to the leg unit. By a "leg bending plane" is in particular a plane to be understood that is spanned by the leg unit, in particular the upper leg part and the lower leg part, and in particular in a state in which the sitting angle differs from 180°, like for example in a sitting posture. Alternatively or additionally the bearing unit could translationally support the foot unit at least substantially orthogonally to the leg bending plane. Preferentially the bearing unit supports at least the portion of the leg unit exclusively parallel to the leg bending plane. In particular as the portion of the foot unit, preferably the shoe adapter and/or the shoe connector of the foot unit are/is translationally supported, at least substantially parallel to the leg bending plane, by the bearing unit.

Furthermore it is proposed that the bearing unit has a first main extension in a first bearing position and has in a second bearing position a second main extension, which is greater than the first main extension. Advantageously a user comfort may be further improved. In particular, a user's freedom of movement is further improvable in this way. A "main extension" of an object is herein in particular to mean a longest edge of a smallest geometrical rectangular cuboid just still completely enclosing the object. A "main extension direction" of an object is here in particular to mean a direction extending parallel to a main extension of the object. The bearing unit is in particular implemented to be expandable and/or contractible. Preferably the bearing unit is fully contracted in the first bearing position. Furthermore the bearing unit is preferably fully expanded in the second bearing position. The second main extension of the bearing unit in the second bearing position is greater than the first main extension of the bearing unit in the first bearing position in particular at least by 5%, preferentially at least by 10%, particularly preferentially at least by 30% and very particularly preferably at least by 50%. In particular, for an expansion of the bearing unit at least the further bearing element is extractable along the bearing element of the bearing unit. In particular, the second main extension of the bearing unit in the second bearing position at least substantially corresponds to the total of the respective main extensions of the bearing element, in particular the guide element of the bearing element, and the further bearing element, in particular the further guide element of the further bearing element, of the bearing unit. Preferably the bearing unit is in the first bearing position arranged at least partly, preferably at least to a large extent and particularly referably completely within a housing. In particular, the foot unit comprises the housing, which is advantageously formed by the foot support.

It is moreover proposed that the bearing unit is at least partly, preferably at least to a large extent, particularly preferably completely expandable at least in one expansion direction away from the leg unit. Comfort may advantageously be improved. Especially advantageously it is avoidable that in an expansion, and thus in particular a positioning of a foot of the person, this is blocked by the leg unit. This therefore advantageously allows further improving operational safety. In particular, the further bearing element is extractable along the bearing element. By an "expansion direction" is in particular a direction to be understood in which the bearing unit is expandable, in particular expandable from the first bearing position into the second bearing position. The bearing unit is in particular at least partly, preferably at least to a large extent and particularly preferably completely contractible at least in a contraction direction towards the leg unit. For this purpose the further bearing element can be pulled in along the bearing element. By a "contraction direction" is in particular a direction to be understood in which the bearing unit is contractible, in particular contractible from the second bearing position into the first bearing position. In particular, the expansion direction and the contraction direction are oriented counter to one another, preferentially anti-parallel.

For the purpose of in particular improving a compactness of a construction shape, it is further proposed that the bearing unit comprises at least one telescopic pull-out. In particular, the bearing element and the further bearing element implement the telescopic pull-out. It is conceivable that the bearing unit comprises a plurality of telescopic pull-outs, which are implemented by further bearing elements and are arrangeable such that they are nested into one another. In particular, if there is a plurality of telescopic pull-outs, it is conceivable that a second main extension in the second bearing position of the bearing unit is greater than the first main extension in the first bearing position of the bearing unit by at least 100%, preferably by at least 150% and particularly preferably by at least 200%.

It is also proposed that the bearing unit comprises at least one reset element, which is configured, in at least one bearing position, in particular in a bearing position that differs from the first bearing position, to at least partially apply a reset force to the foot unit. Further improving of comfort is advantageously possible. In particular, an undesired activation of the bearing unit is advantageously avoidable. Furthermore a specified resetting of the bearing unit may be effected advantageously. Especially advantageously it is possible to generate a physiological movement process. The reset element is in particular realized as an elastic element. By an "elastic element" is in particular an element to be understood which is repeatedly deformable without being mechanically damaged or destroyed and which in particular, following a deformation, automatically seeks to re-assume its basic shape. Preferentially the elastic element is embodied as a spring, like preferably a spiral spring. Alternatively or additionally the elastic element could be embodied as a rubber band. The reset element is in particular connected with at least one bearing element, in particular the further bearing element, of the bearing unit. Preferably the reset element is connected at least with the further bearing element. Alternatively or additionally the reset element may be connected with a further structural component, for example the foot unit, in particular the foot unit support, the ground contact unit, the leg unit, or the like. In particular, in at least one bearing position that differs from the first bearing position, preferentially the second bearing position, the reset element exerts a reset force that is directed at least transversely to the longitudinal leg axis, in particular the upper longitudinal leg axis and/or the lower longitudinal leg axis, and preferably at least substantially parallel to the leg bending plane.

Beyond this it is proposed that in at least one bearing position of the bearing unit, in particular in the first bearing position of the bearing unit, the reset element is arranged in such a way that it is overlapped at least partly, preferably at least to a large extent and particularly preferably completely, in particular when viewed in a direction at least substantially parallel to the leg unit. It is advantageously possible to further improve operational safety as contaminations getting into the bearing unit and possibly blocking the bearing unit can be avoided. More advantageously a uniform design is achievable. Preferentially the reset element is arranged at least partly, preferably at least to a large extent and especially preferably completely within the bearing unit, in particular within the bearing element and/or the further bearing element. Particularly preferably the reset element is arranged between the bearing element and the further bearing element. In particular, the further bearing element has a recess which the reset element is arranged in at least partly. Furthermore the reset element is overlapped at least partly, preferably at least to a large extent and particularly preferably completely by the foot unit, in particular the foot unit support.

It is also proposed that the bearing unit comprises at least one delimitation element, which is configured to delimit a translational movement of the portion of the foot unit. The delimitation element in particular comprises a main extension direction having at least one component that is oriented substantially orthogonally to a guiding direction of the bearing unit. Advantageously a malfunctioning of the bearing unit is avoidable, for example if the further bearing element is completely pulled out along the bearing element. In particular, a particularly preferred arrangement is achievable and/or a construction space is reducible and further structural components may be done without if it is proposed that the delimitation element is realized at least partly integrally with at least one bearing element, in particular the above-mentioned bearing element and/or the above-mentioned further bearing element. Alternatively or additionally the delimitation element may be realized at least partly by the foot unit, for example by the foot unit support, the shoe adapter or the like.

In particular for further improvement of comfort, it is proposed that the bearing unit comprises at least one bearing element and at least one further bearing element, namely in particular the above-mentioned bearing element and the above-mentioned further bearing element that is embodied correspondingly to the bearing element, the main extension directions of the bearing elements being oriented transversely to the longitudinal leg axis, in particular the upper longitudinal leg axis and/or the lower longitudinal leg axis, and preferentially substantially parallel to the leg bending plane.

Furthermore it is proposed that in at least one bearing position, in particular in the above-mentioned first bearing position, the bearing element and the further bearing element are arranged at least partly, preferably at least to a large extent and particularly preferably completely within one another. It is advantageously possible for a safety to be further improved. In particular, the bearing element is at least partly, preferably at least to a large extent and particularly preferably completely arranged in the further bearing element. Preferentially the bearing element is at least partly engaged around by the further bearing element, in particular from at least two sides, preferably from at least three sides.

In particular for the purpose of further improving ergonomics, it is moreover proposed that the bearing unit is arranged at an end section of the leg unit. By an "end section" is in particular a section to be understood which extends from a free and open end of a component along a direction of the component over a length of maximally 30%, preferably no more than 15% and particularly preferably maximally 5% of a main extension of the component. Preferentially the bearing unit is arranged on an end section of the lower leg part of the leg unit. The bearing unit is in particular arranged on the foot unit support and/or on the ground contact unit. The foot unit support and/or the ground contact unit are in particular arranged on the end section of the leg unit, preferably of the lower leg part of the leg unit.

Beyond this it is proposed that the bearing unit is implemented at least partly, preferably at least to a large extent and particularly preferably completely integrally with the foot unit. This advantageously allows reducing expenses as well as dispensing with further structural components. It is further possible to achieve a uniform appearance. Especially advantageously a stability of the foot unit and in particular of the bearing unit are/is improvable. In particular, at least one further bearing element of the bearing unit is implemented at least partly, preferably at least to a large extent and particularly preferably completely integrally with the shoe adapter. In particular, the bearing element is implemented at least partly, preferably to a large extent and particularly preferably completely integrally with the foot unit support.

It is further proposed that the foot unit comprises at least one at least partially rubber-elastic joint unit, which is in particular formed at least partially of an elastomer, for a connection to the leg unit. In particular, the joint unit comprises at least one joint base body, which is implemented to be rubber-elastic. By the joint unit, in particular the joint base body, being implemented to be "rubber-elastic" is in particular to be understood that the joint unit, in particular the joint base body, is deformable relative to its basic shape by forces acting onto the joint unit, in particular the joint base body, during a use of the wearable sitting-posture assisting device, in particular while a user is walking with the wearable sitting-posture assisting device and/or while a user is sitting on the wearable sitting-posture assisting device, wherein the joint unit, in particular the joint base body, will, in particular autonomously, re-assume its basic shape in a load-free state. In particular, the joint unit, in particular the joint base body, is implemented such that it is deformable differently than plastically deformable, in particular elastically deformable, under an impact of forces acting onto the joint unit, in particular the joint base body during a use of the wearable sitting-posture assisting device. The joint unit, in particular the joint base body, is preferably connected at least with a further portion of the foot unit, in particular the foot unit support and/or the bearing unit, in particular by a form-fit and/or force-fit connection. The joint base body is preferably embodied as an at least substantially L-shaped, respectively C-shaped, structural component. Alternatively other ways of shaping the joint base body, which are in particular deemed expedient by someone skilled in the art, are also conceivable. Preferentially the leg unit, in particular the lower leg support, extends through the joint unit, in particular through a pass-through in the joint base body. In particular, the leg unit, in particular the lower leg support, is coupled with the joint unit, in particular indirectly via at least one coupling element of the foot unit. The joint base body is preferably made of an elastomer, in particular a rubber. Alternatively it is conceivable that the joint base body is made of a material that differs from an elastomer, and in particular comprises at least one rubber-elastic and/or shock-absorbing component, like for example a spring element, a pneumatic damper, an hydraulic damper, a shape-memory metal, or the like.

Preferentially the joint unit, in particular the joint base body, is implemented to be elastically deformable in a rotational and/or translational manner. Preferably the joint base body is implemented to be elastically deformable rotationally around a first rotation axis that extends at least substantially parallel to the contraction direction of the bearing unit. In particular, a rotation of a foot connected to the foot unit around the first rotation axis at least substantially corresponds to a pronation respectively a supination of the foot. Preferentially the joint base body is implemented to be elastically deformable rotationally around a second rotation axis that extends at least substantially orthogonally to the contraction direction of the bearing unit and at least substantially orthogonally to the longitudinal leg axis, in particular the lower longitudinal leg axis. In particular, a rotation of a foot connected with the foot unit around the second rotation axis at least substantially corresponds to a flection respectively an extension of the foot. Preferably the joint base body is implemented to be elastically deformable rotationally around a third rotation axis extending at least substantially parallel to the longitudinal leg axis, in particular the lower longitudinal leg axis. Preferentially the joint base body is implemented to be elastically deformable translationally along any desired movement axes, in particular at least substantially orthogonally and/or at least substantially parallel to the rotation axes. In particular, the joint base body is configured for a damping, in particular a damping by a rubber-elasticity of the joint base body, of oscillations occurring during a use of the wearable sitting-posture assisting device, in particular while a user is walking with the wearable sitting-posture assisting device. In particular, the joint unit, in particular the joint base body, is implemented to be rubber-elastic in such a way that, under a load of maximally 100 N, preferentially no more than 70 N, especially preferentially maximally 50 N and very particularly preferentially maximally 30 N, the joint unit, in particular the joint base body, is deformable, in particular translationally deformable, by a maximum extent between 0.1 cm and 7 cm, preferably between 0.1 cm and 5 cm, particularly preferably between 0.1 cm and 3 cm and very particularly preferably between 0.1 cm and 2 cm relative to its basic shape. In particular, the joint unit, in particular the joint base body, is implemented to be rubber-elastic in such a way that, under a load of maximally 100 N, preferably maximally 70 N, particularly preferably no more than 50 N and very especially preferentially no more than 30 N, the joint unit, in particular the joint base body, is rotationally deformable by a maximum rotation angle between 5° and 60°, preferably between 5° and 45°, particularly preferably between 5° and 30°, and particularly preferably between 5° and 20° relative to its basic shape. Advantageously an oscillation damping may be enabled during a use of the wearable sitting-posture assisting device. Advantageously it is possible to provide a user-friendly wearable sitting-posture assisting device, which is in particular usable in a low-noise and low-wear manner.

Beyond this it is proposed that the foot unit comprises at least one buffer element, which is configured for an impact damping of at least a portion of the foot unit and/or of the bearing unit which a reset force has been applied to and which is in particular contracting. The at least one buffer element is preferably connected with the joint unit, and is in particular implemented integrally with the joint base body. Preferentially the at least one buffer element is embodied to be rubber-elastic. In particular, the at least one buffer element is made of the same material as the joint base body, in particular of an elastomer. Alternatively it is conceivable that the at least one buffer element is made of a material that differs from a material of the joint base body. In particular, the at least one buffer element is arranged in a connection region of the joint base body with a portion of the foot unit, in particular with the foot unit support, and/or with the bearing unit. Preferably the at least one buffer element serves as an end abutment of the further bearing element in the first bearing position of the foot unit. In particular, the at least one buffer element is configured for damping an impact of the further bearing element onto the joint base body, wherein a reset force has been applied to the further bearing element by the reset element and the further bearing element is in particular accelerated along the contraction direction. In particular, the at least one buffer element has shock-absorbing characteristics. Preferably the at least one buffer element is implemented to be elastically deformable by a force acting onto the at least one buffer element due to the impact of the further bearing element. Preferentially the foot unit comprises a plurality of buffer elements. In particular, the foot unit comprises at least two buffer elements, which are in particular arranged spaced apart from one another along a direction extending at least substantially orthogonally to the contraction direction, in particular arranged on the joint base body. It is advantageously possible to provide a wearable sitting-posture assisting device with a low-noise and low-wear foot unit permitting a high level of wearing comfort.

It is further proposed that the joint unit is clearance-free connected, in particular pressed, with at least a portion of the foot unit and/or of the bearing unit. Preferentially the joint unit, in particular the joint base body, is in a form-fit connection with at least a portion of the foot unit and/or of the bearing unit. Preferably the joint unit, in particular the joint base body, is clearance-free connected, in particular pressed, with the bearing element and/or with the guide rail of the bearing unit. Alternatively or additionally it is conceivable that the joint unit, in particular the joint base body, is clearance-free connected, in particular pressed, with at least a portion of the foot unit, in particular with the foot unit support. Preferentially the bearing element and/or the guide rail are/is pressed into the joint base body, in particular into a receiving opening that is delimited by the joint base body. Preferably the bearing element and/or the guide rail have/has at least section-wise, in particular in a section extending within the joint base body, a fir-tree geometry, in particular for an implementation of a press connection with the joint base body. Preferentially, the bearing element and/or the guide rail have in the section extending within the joint base body, in particular rib-like, projections for an implementation of a clearance-free, in particular rotationally fixed, connection with the joint base body. In particular, the projections realize the fir-tree geometry of the bearing element and/or the guide rail. Preferably the projections are arranged in poka-yoke fashion, in particular for a realization of a pre-determined orientation of the bearing unit relative to the joint unit, in particular to the joint base body. By the projections being arranged "in poka-yoke fashion" is in particular to be understood that the projections are arranged in such a way that the projections enable a connection of the bearing element and/or the guide rail with the joint unit, in particular the joint base body, in one single, in particular pre-determined orientation relative to the joint unit, in particular to the joint base body. It is advantageously possible to provide a wearable sitting-posture assisting device that has few structural components and is easily mountable, featuring a high level of operational and/or usage safety.

Furthermore it is proposed that the foot unit comprises at least one coupling element which is connected with the joint unit, which the leg unit extends through at least section-wise and which has material properties differing from the joint unit, in particular a material that has a higher hardness than the joint unit. The coupling element is preferably embodied as a coupling sleeve. In particular, the coupling element is connected with the joint base body. Preferentially the coupling element is arranged in the joint base body at the pass-through, and in particular extends through the pass-through in the joint base body. Preferably the coupling element is made of a harder material than the joint base body. In particular, the coupling element has a lower elasticity than the joint base body. Preferentially the coupling element is implemented to be at least substantially non-deformable by forces, in particular a force of maximally 100 N, acting onto the coupling element during a use of the wearable sitting-posture assisting device, and in particular to be deformable by a maximum extent of no more than 1 mm relative to a load-free basic shape of the coupling element. The coupling element is preferably made of a synthetic material, in particular a thermoset material. Alternatively it is conceivable that the coupling element is made of a metal, of a composite material or of another material that is deemed expedient by someone skilled in the art. In particular, the coupling element is made of a material that differs from an elastomer, in particular from a rubber. The joint base body, which is in particular implemented of an elastomer, is preferably connected with the coupling element at least by substance-to-substance bond, in particular by vulcanization. Alternatively it is conceivable that the joint base body is connected with the coupling element by gluing, by latching, by pressing or by another kind of connection that is deemed expedient by someone skilled in the art. The coupling element is preferably configured for a connection with the leg unit, in particular the lower leg support that extends through the coupling element. In particular, the coupling element comprises at least one coupling projection, in particular a coupling pin, for a coupling with the lower leg support. The coupling projection in particular extends into the pass-through that is delimited by the coupling element, respectively by the joint base body. The coupling projection is preferentially configured to enable a movement of the leg unit, in particular the lower leg support, relative to the foot unit, in particular the joint base body. Advantageously it is possible for a material wear of the joint base body caused by the leg unit at to be kept a low level. Advantageously a robust wearable sitting-posture assisting device, in particular having a long lifetime and supplying a high wearing comfort, may be provided.

It is also proposed that the coupling element is embodied as a poka-yoke element. By the coupling element being embodied as a "poka-yoke element" is in particular to be understood that the coupling element features a shaping allowing a connection of the coupling element with the joint unit, in particular the joint base body, in a single, in particular pre-determined orientation relative to the joint unit, in particular the joint base body. In particular, the coupling element comprises orientation projections arranged along a circumferential direction. Preferably an uneven number of orientation projections, in particular one orientation projection, is embodied differently than the remaining orientation projections. Preferentially the coupling element has, in particular along the circumferential direction, a flower-like shaping, in particular with the orientation projections corresponding to imaginary petals of a flower. Preferably the, in particular flower-like, shaping of the coupling element, in particular the orientation projections, implement/s a rotationally fixed securing of the coupling element relative to the joint unit, in particular the joint base body. Preferably the orientation projections have an organic shape. In particular, the orientation projections are implemented to be free of sharp edges and/or corners, in particular rounded. Preferentially the coupling element, in particular the orientation projections, is/are configured, due to the shaping, to keep tensioning between the coupling element and the joint unit, in particular the joint base body, at a low level. Advantageously it is possible to enable a secure and low-wear connection between the coupling element and the joint unit. Advantageously a wearable sitting-posture assisting device with a high level of operational and/or usage safety may be made available.

Furthermore a method for an operation of a wearable sitting-posture assisting device is proposed, in which in at least one method step a foot unit that is configured for a connection of a shoe and/or foot of a person is translationally moved transversely to a longitudinal leg axis defined by a leg unit, in particular an upper longitudinal leg axis and/or a lower longitudinal leg axis It is advantageously possible to improve comfort, in particular a wearing comfort, and/or ergonomics.

It is proposed that the leg unit defines at least one leg bending plane, relative to which the shoe adapter and the shoe connector are couplable at least substantially orthogonally. Advantageously comfort, in particular a wearing comfort, may be further improved. It is in particular possible to avoid a user's foot getting inadvertently decoupled in a movement parallel to the leg bending plane, which may occur when walking or also when moving while sitting. This in particular also allows improving operational safety. Alternatively or additionally the shoe adapter and the shoe connector could be couplable at least substantially parallel to the leg bending plane. Preferentially the shoe adapter and the shoe connector are couplable exclusively at least substantially orthogonally to the leg bending plane.

It is further proposed that the quick coupling is configured at least for a force-fit and/or form-fit coupling of the shoe adapter and the shoe connector. It is advantageously possible to further improve comfort. In particular, a combination of coupling mechanisms allows providing a quick coupling that is stable and easy to be handled. The quick coupling preferentially comprises at least one quick coupling element that is configured for a force-fit and/or form-fit connection. Particularly preferably the quick coupling is embodied thread-less and/or free of a bayonet connection.

It is also proposed that the quick coupling comprises at least one magnet element, which is configured at least partially to realize a coupling of the shoe adapter with the shoe connector. It is advantageously possible to further improve comfort, in particular operating comfort. In particular, this allows simplifying a positioning of the shoe adapter relative to the shoe connector and/or a coupling of the shoe adapter and the shoe connector. A "magnet element" is in particular to mean a permanent magnetic and/or magnetizable element. The magnet element is in particular implemented at least partly, preferably to a large extent and particularly preferably completely, of a ferromagnetic, preferably soft-magnetic material and/or of a hard-magnetic material, like for example iron, nickel, cobalt or the like. Especially preferentially the magnet element is permanent magnetic. In particular, the further quick coupling element comprises the magnet element. In particular, the quick coupling element may be implemented at least partly integrally with the magnet element. For example, the latch element of the quick coupling element could be implemented integrally with the magnet element. Furthermore the quick coupling in particular comprises at least one further magnet element, which is preferably embodied correspondingly to the magnet element. For example, the further magnet element is implemented and/or arranged in such a way that in a coupling process different magnetic poles of the magnet element and the further magnet element face each other and therefore mutually attract each other. The further magnet element is preferably magnetizable. The further quick coupling element in particular comprises the further magnet element. Moreover the further quick coupling element could be embodied at least partly integrally with the further magnet element. Preferentially, the further latch element of the further quick coupling element could for example be embodied integrally with the further magnet element. Preferably at least one, in particular only one, of the magnet elements is made of a hard magnetic material. The magnet element, in particular in an interaction with the further magnet element, is in particular configured to generate a magnetic attracting force which moves at least the shoe adapter and at least the shoe connector towards each other at least transversely to the longitudinal leg axis, in particular the upper longitudinal leg axis and/or the lower longitudinal leg axis, and preferably transversely to the leg bending plane.

It is moreover proposed that the magnet element is configured for activating a coupling of the shoe adapter with the shoe connector via the latch element. Advantageously it is possible to further improve comfort as in particular an effortful activation by the quick coupling, for example with stooping down, is avoided. In particular, the magnet element, in particular in an interaction with the further magnet element, generates a magnetic attracting force that is configured to deflect the latch element, thus latching the latch element with the further latch element. In particular in a coupled state of the shoe adapter with the shoe connector, the coupling is generated at least partially by a magnetic force-fit connection and/or at least partially by a force-fit and/or form-fit latch connection.

Furthermore it is proposed that the quick coupling supports the shoe adapter and the shoe connector around a rotation axis transversely to the longitudinal leg axis, in particular the upper longitudinal leg axis and/or the lower longitudinal leg axis. It is advantageously possible to improve comfort, ergonomics and/or physiology. Especially advantageously the rotation axis permits a natural movement sequence of the foot, allowing an angling of the foot when walking and/or sitting. In particular, the quick coupling element forms at least one axle. The further quick coupling element in particular at least partially forms an axle receptacle that is embodied correspondingly to the axle. The axle is in particular arrangeable in the axle receptacle. The rotation axis is preferably defined by the main extension direction of the axle and/or of the axle receptacle.

It is further proposed that the wearable sitting-posture assisting device comprises at least one quick release unit, which is configured to release the shoe adapter and the shoe connector from each other without a tool. Advantageously comfort and safety can be further improved. By a "quick release unit" is in particular a unit to be understood which is configured for a decoupling of a coupling of two components generated by the quick coupling, said decoupling being effected in a tool-less, non-destructive and/or repeatable, preferably one-handed, one-legged and/or one-footed manner, especially advantageously by a single movement of a hand, a foot and/or a leg of a person. Preferentially the quick release unit is configured to undo a latching of the latch elements and/or to space the magnet elements apart from each other, as a result of which their mutual magnetic interaction substantially disappears.

Beyond this it is proposed that the quick release unit comprises at least one actuation element for a decoupling of the shoe adapter and the shoe connector. Advantageously comfort can be further improved. Especially advantageously, in this way a desired decoupling may be specifically activated, and in particular tool-lessly activated. The actuation element is preferably embodied as a pull handle, which is in particular capable of being moved, in particular pulled out and/or pushed inward, relative to the shoe adapter and/or to the shoe connector. Alternatively or additionally the actuation element could be embodied as an operating lever and/or operating bar.

It is also proposed that in an actuation the actuation element displaces the latch element relative to the magnet element at least indirectly. Advantageously safety may be improved as a decoupling can only be initiated by specific activation. "At least indirectly" is in particular to mean indirectly and/or directly. In particular, the quick release unit may comprise at least one transmission mechanism that is configured for displacing the latch element relative to the magnet element.

It is moreover proposed that the actuation element can be actuated at least substantially parallel to the longitudinal leg axis, in particular the upper longitudinal leg axis and/or the lower longitudinal leg axis. An operating comfort can be further improved as the actuation element is particularly easily accessible for a person wearing the sitting-posture assisting device.

The invention further relates to a foot unit of a wearable sitting-posture assisting device according to the invention.

Furthermore a method for an operation of the wearable sitting-posture assisting device is proposed, in which in at least one method step at least the shoe adapter and at least the shoe connector are coupled with each other at least transversely to the at least one longitudinal leg axis, in particular the upper longitudinal leg axis and/or the lower longitudinal leg axis, of the leg unit, wherein the quick coupling couples the shoe adapter and the shoe connector with each other without a tool, wherein the at least one latch element of the quick coupling at least partially realizes the coupling of the shoe adapter with the shoe connector. It is advantageously possible to improve comfort, in particular a wearing comfort, and/or ergonomics.

The wearable sitting-posture assisting device according to the invention, the foot unit according to the invention and/or the method for an operation of the wearable sitting-posture assisting device according to the invention are/is here not to be restricted to the application and implementation described above. In particular, for the purpose of fulfilling a functionality that is described here, the wearable sitting-posture assisting device according to the invention, the foot unit according to the invention and/or the method for an operation of the wearable sitting-posture assisting device according to the invention may comprise a number of individual elements, structural components and units as well as method steps that differs from a number that is mentioned herein. Moreover, concerning the value ranges given in the present disclosure, values situated within the limits named are also to be considered as disclosed and as insertable according to any requirements.

DRAWINGS

Further advantages will become apparent from the following description of the drawings. The drawings show two exemplary embodiments of the invention. The drawings, the description and the claims contain a plurality of features in combination. Someone skilled in the art will purposefully also consider the features individually and will find further expedient combinations.

Figure 2:
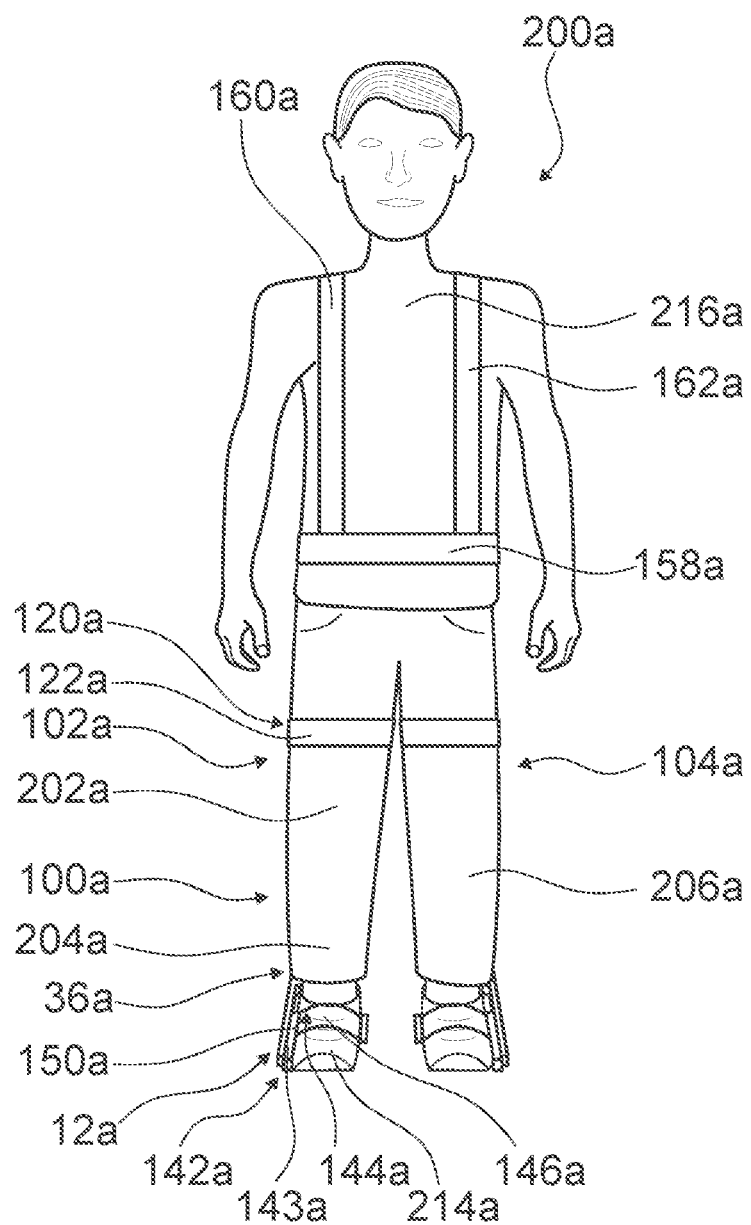
Figure 3:
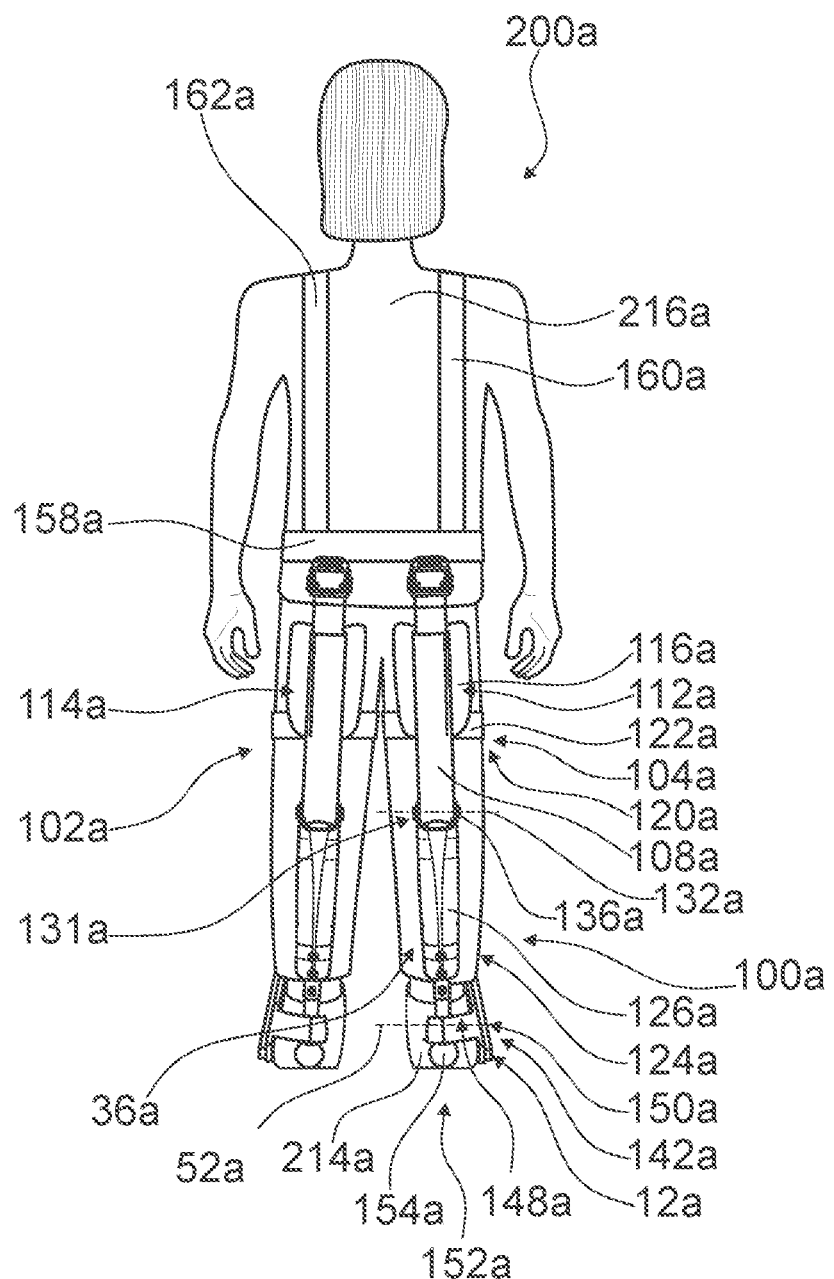
Figure 4:
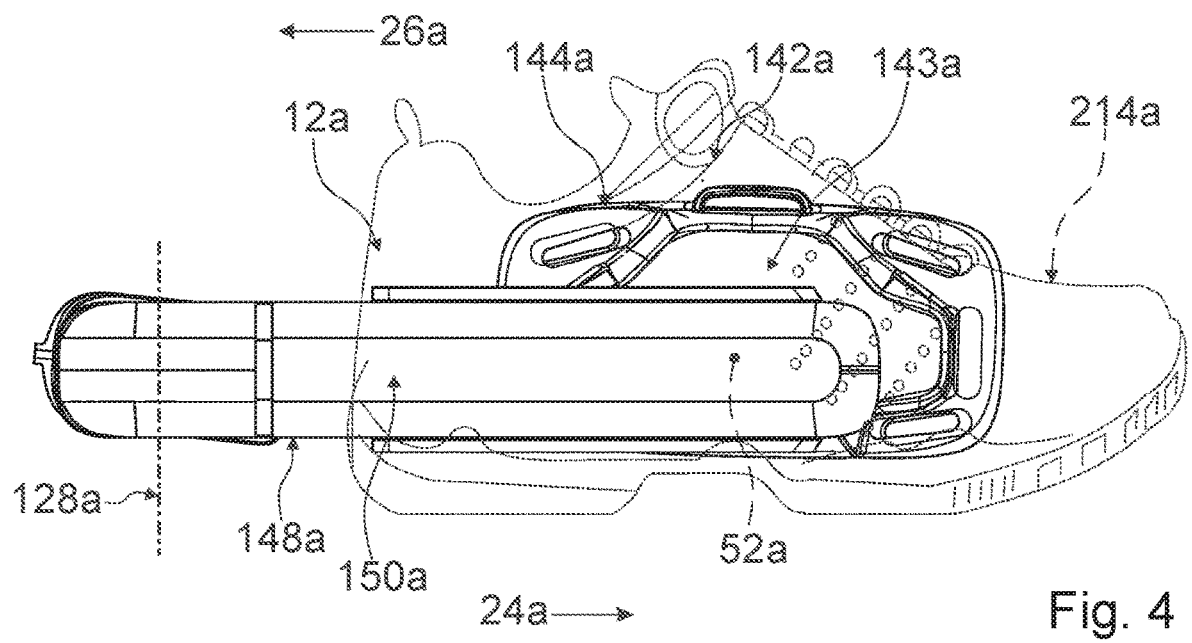
Figure 5:
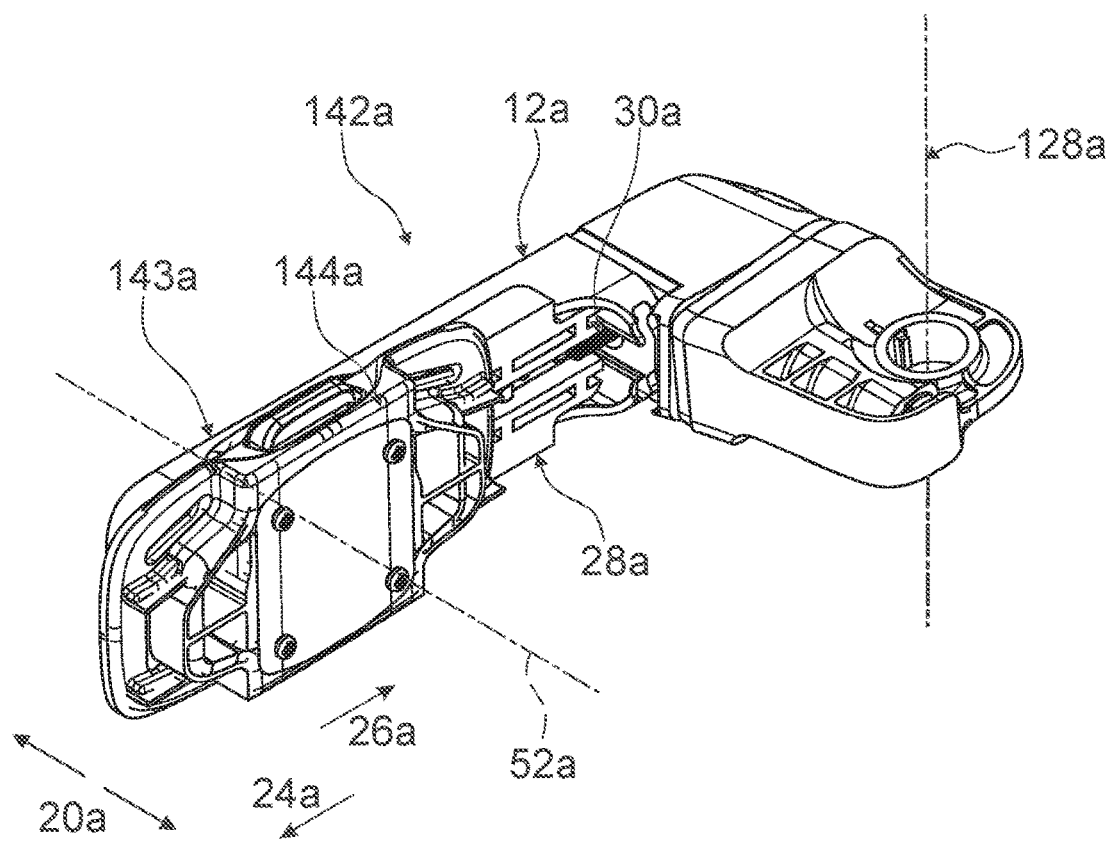
Figure 6:
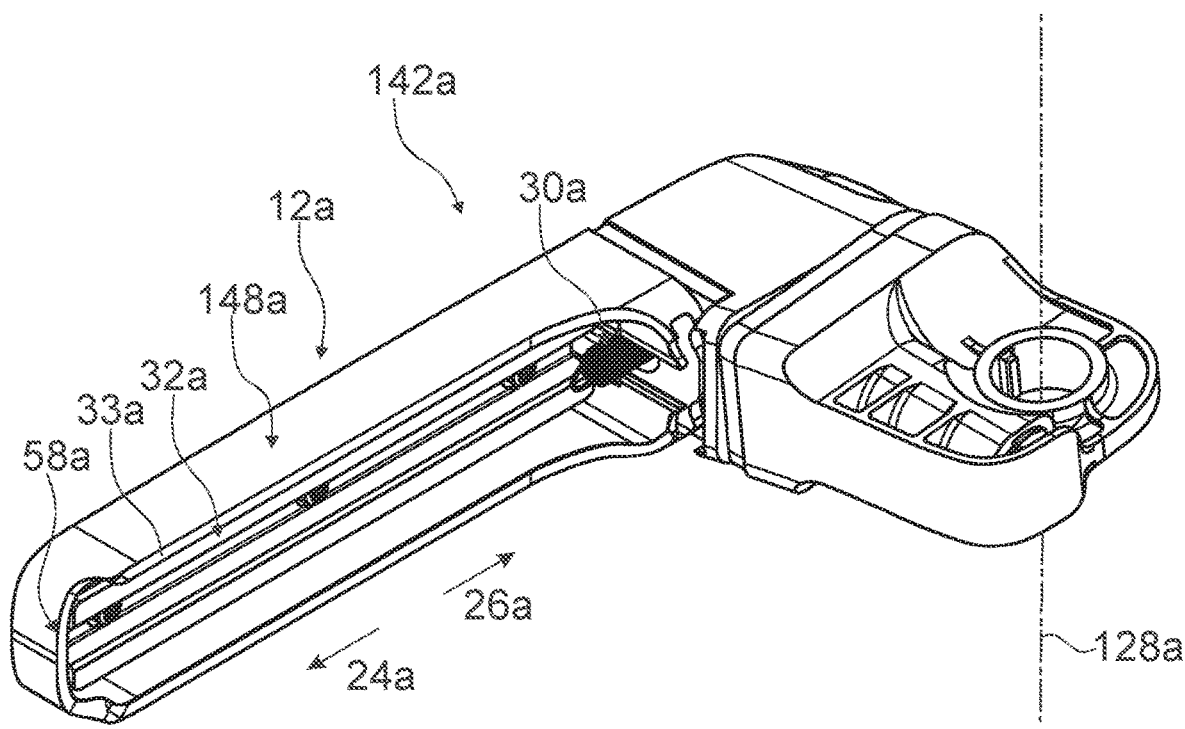
Figure 7:
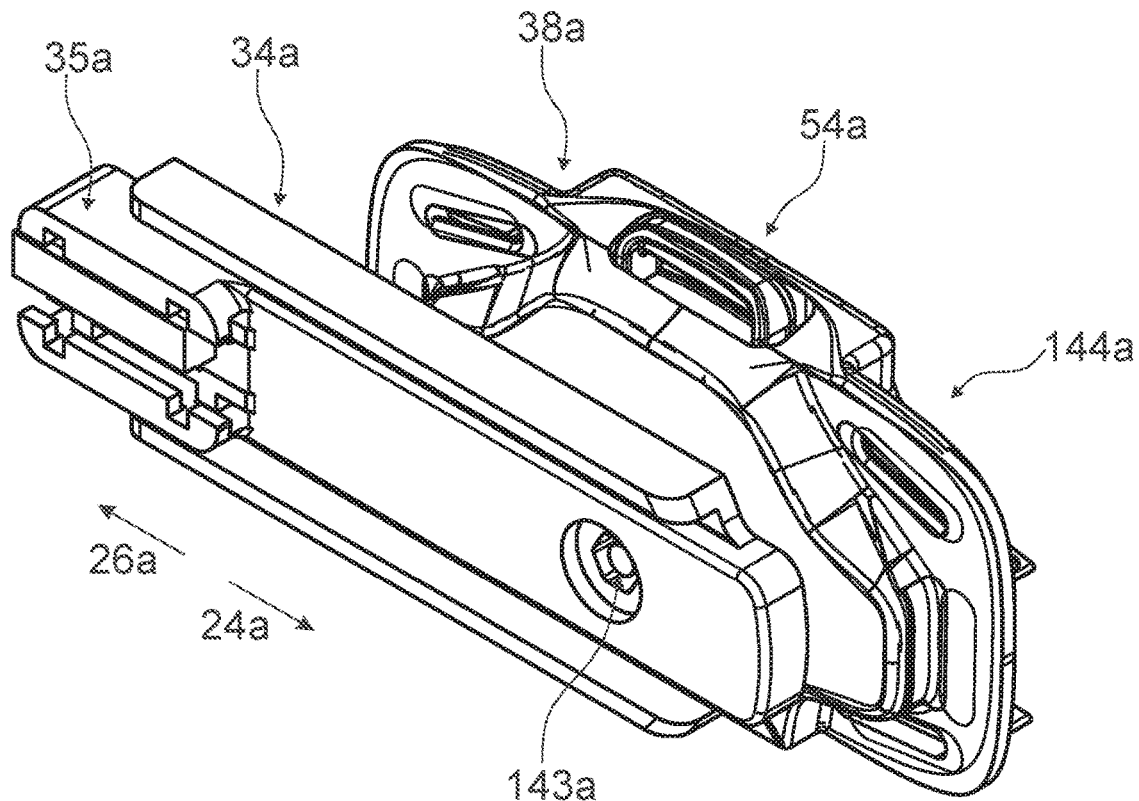
Figure 8:
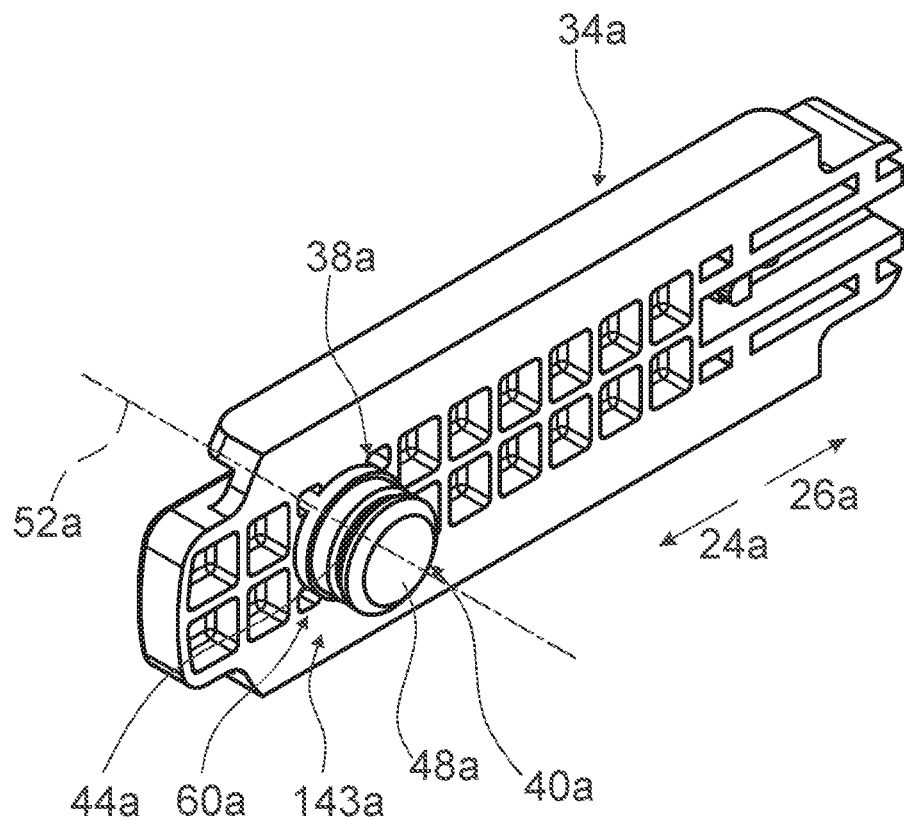
Figure 9:
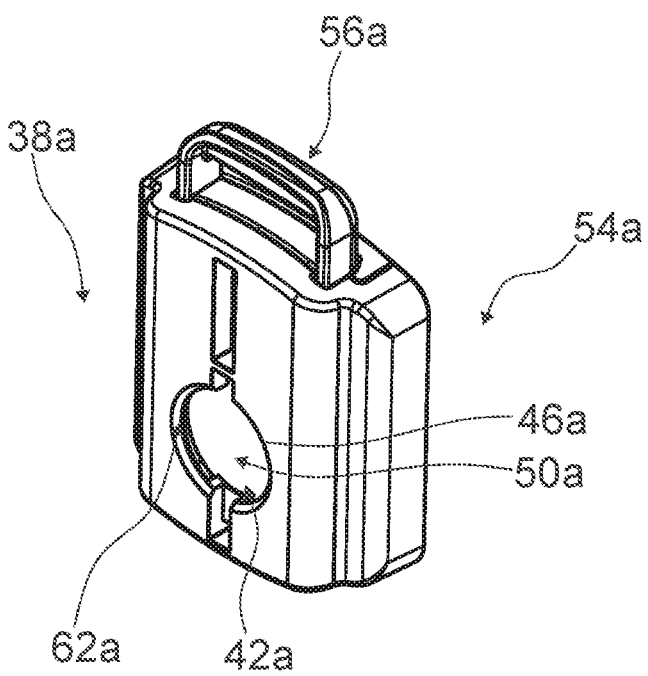
Figure 10:
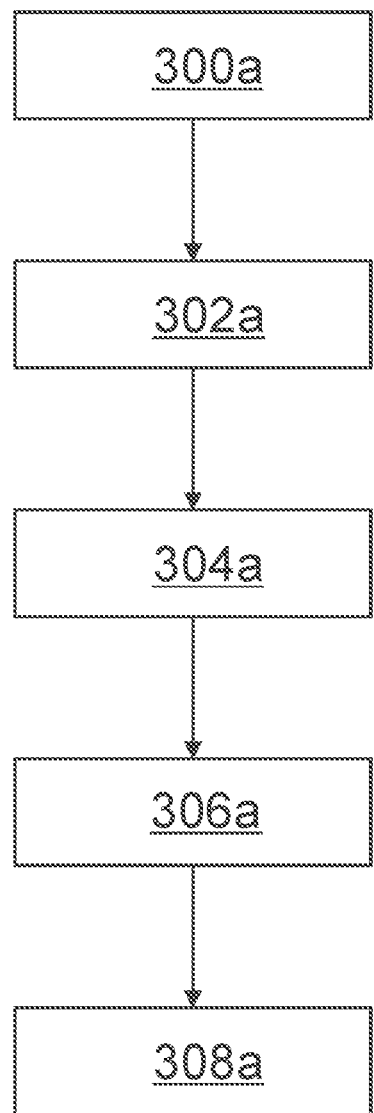
Figure 11:
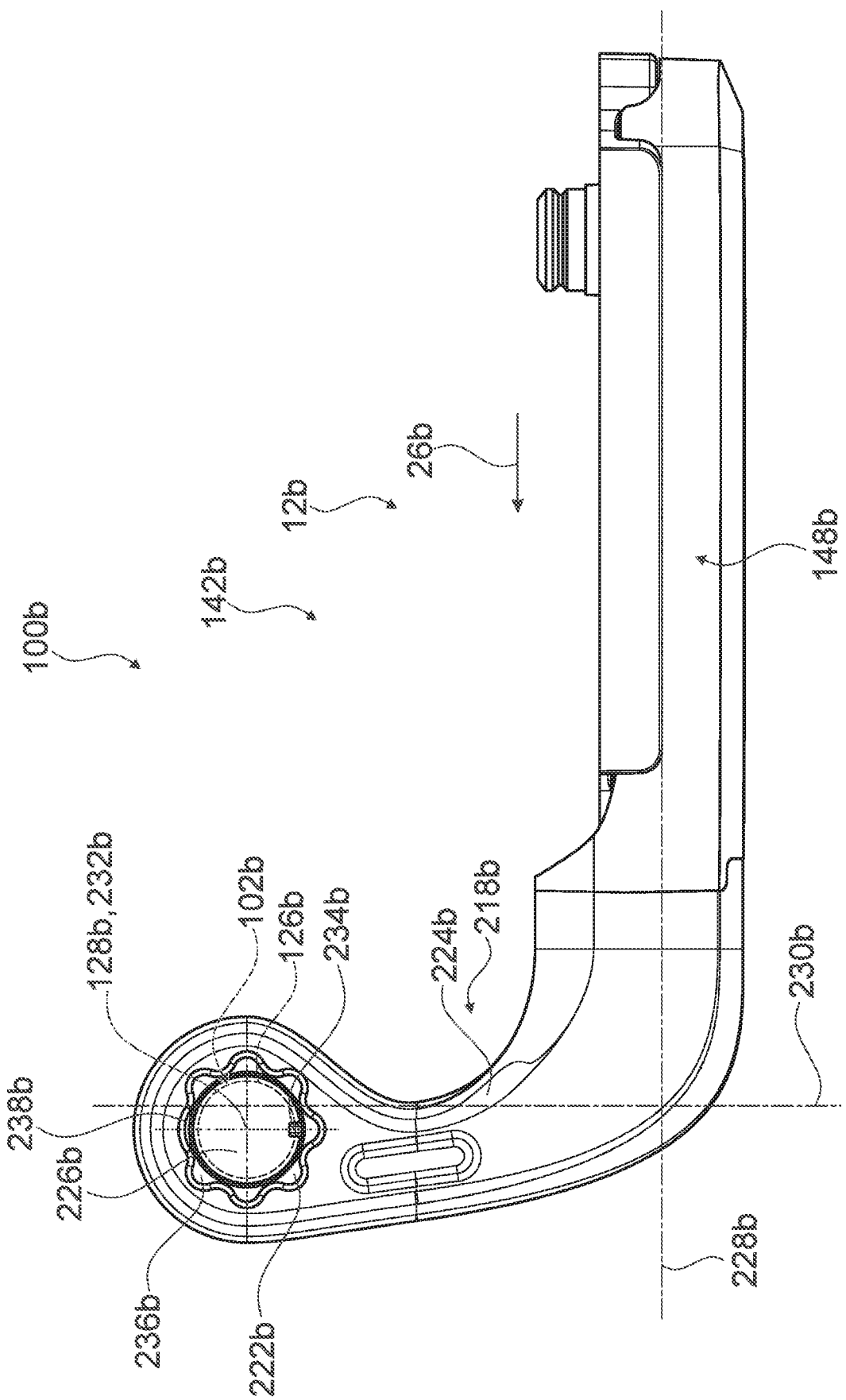
Figure 12:
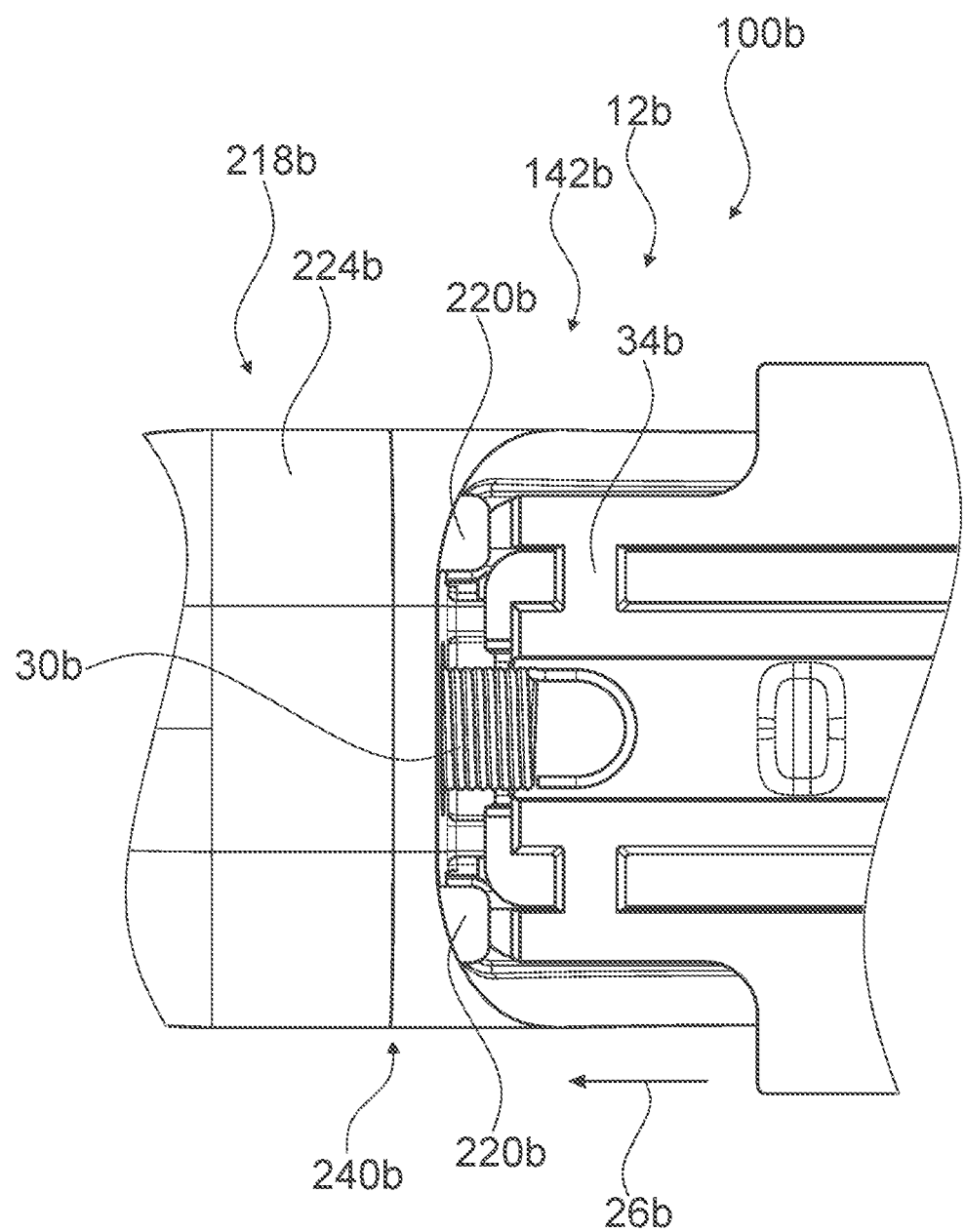
Figure 13:
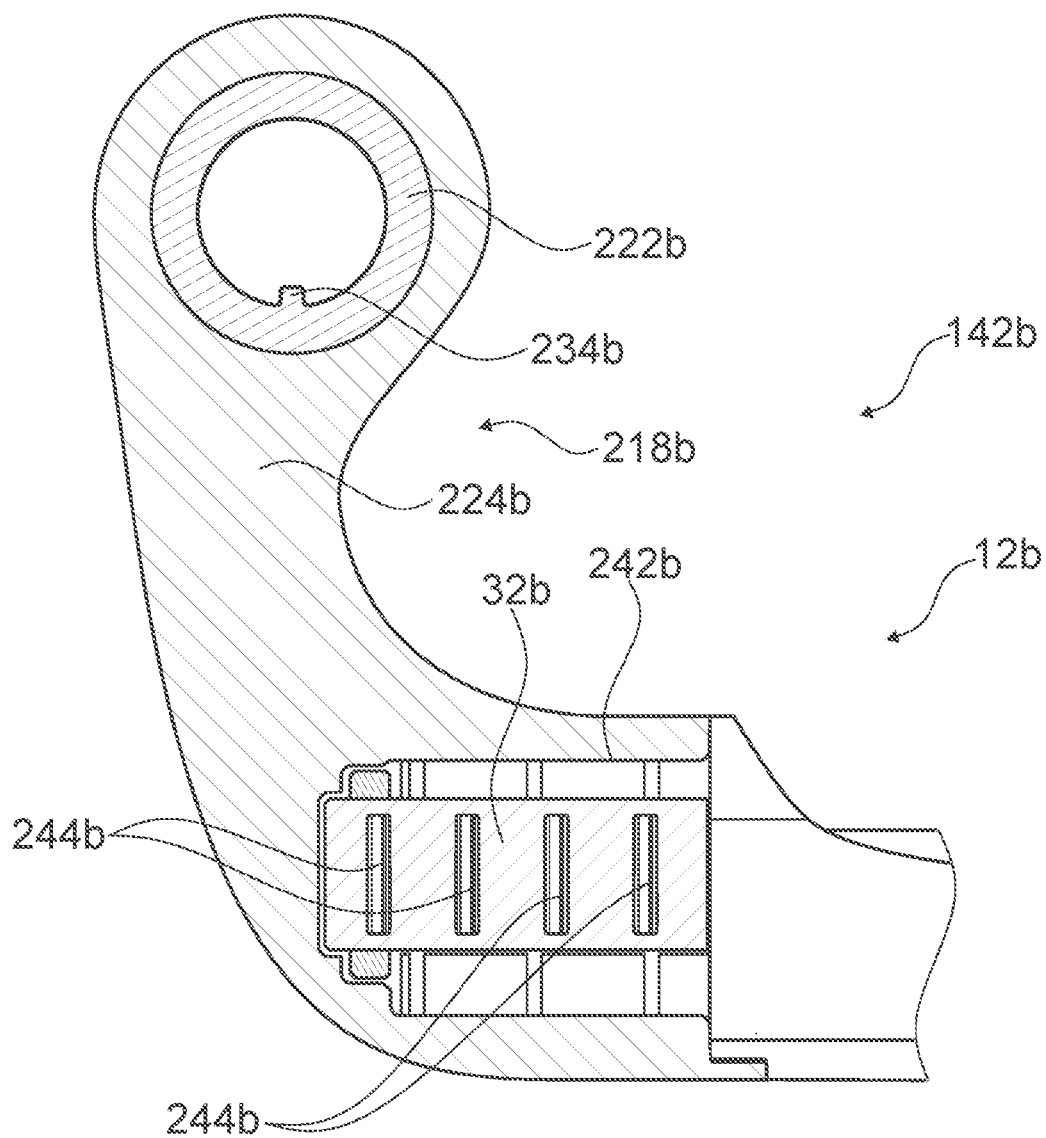

It is shown in:

FIG. 1 a person with a wearable sitting-posture assisting device in a schematic side view, FIG. 2 the wearable sitting-posture assisting device in a schematic front view, FIG. 3 the wearable sitting-posture assisting device in a schematic view from the rear, FIG. 4 a portion of the wearable sitting-posture assisting device with a foot unit and a bearing unit, in a schematic side view, FIG. 5 a portion of the wearable sitting-posture assisting device with the foot unit and the bearing unit, in a perspective view, FIG. 6 a portion of the wearable sitting-posture assisting device with a bearing element of the bearing unit, in a perspective view, FIG. 7 a portion of the wearable sitting-posture assisting device with a quick coupling and a further bearing element of the bearing unit, in a perspective view, FIG. 8 the further bearing element and a portion of the quick coupling, FIG. 9 a portion of the foot unit and a portion of the quick coupling, FIG. 10 a schematic flow chart of a method for an operation of the wearable sitting-posture assisting device, FIG. 11 a portion of an alternative wearable sitting-posture assisting device in a schematic view, FIG. 12 a portion of the alternative wearable sitting-posture assisting device of FIG. 11 in a further schematic view, and FIG. 13 a portion of the alternative wearable sitting-posture assisting device of FIG. 11 in a schematic sectional view.

DESCRIPTION OF THE EXEMPLARY EMBODIMENTS

FIG. 1 shows a person 200a wearing a wearable sitting-posture assisting device 100a. The wearable sitting-posture assisting device 100a is configured to receive a weight force of the person 200a in a sitting posture or in a partial sitting posture. In FIG. 1 the person 200a is illustrated in a partial sitting posture. In the partial sitting posture a knee 202a of the person 200a is partly bent. In a sitting posture the knee 202a is bent to a higher degree than in the partial sitting posture. The wearable sitting-posture assisting device 100a is configured to enable the person 200a to sit down on the wearable sitting-posture assisting device 100a in different sitting postures and to partly sit down on the wearable sitting-posture assisting device 100a in different partial sitting postures. The wearable sitting-posture assisting device 100a is furthermore configured to enable the person 200a to walk while wearing the wearable sitting-posture assisting device 100a. The wearable sitting-posture assisting device 100a is moreover configured to enable the person 200a to stand and/or to get up and/or to sit down and/or to walk while wearing the wearable sitting-posture assisting device 100a.

FIG. 2 shows the person 200a wearing the wearable sitting-posture assisting device 100a in a schematic front view. FIG. 3 shows the person 200a wearing the wearable sitting-posture assisting device 100a in a schematic view from the rear. In FIGS. 1 to 3 the wearable sitting-posture assisting device 100a is shown in a normal wearing state. The normal wearing state comprises a state in which the person 200a is sitting on the wearable sitting-posture assisting device 100a, a state in which the person 200a is partly sitting, a state in which the person 200a is sitting down, a state in which the person 200a is standing and a state in which the person 200a is walking, in each case with the person 200a wearing the wearable sitting-posture assisting device 100a. In the illustrated case the person 200a is wearing the wearable sitting-posture assisting device 100a in a factory building, in particular while working at an assembly line. In a similar way it is conceivable that the person 200a wears the wearable sitting-posture assisting device 100a in an office building, in a service building, in the open, at home, while working, during breaks, etc. Advantageously the person 200a wears the wearable sitting-posture assisting device 100a during an activity that requires the person 200a to repeatedly sit down and/or partly sit down and/or get up and/or stand and/or walk. The person 200a may then, if required, sit down onto the wearable sitting-posture assisting device 100a while wearing the wearable sitting-posture assisting device 100a, may get up, if required, while wearing the wearable sitting-posture assisting device 100a and may walk, if required, while wearing the wearable sitting-posture assisting device 100a.

The wearable sitting-posture assisting device 100a comprises a leg unit 102a. Furthermore the wearable sitting-posture assisting device 100a comprises an additional leg unit 104a. The additional leg unit 104a is implemented identically with the leg unit 102a. Because of this, in the following only the leg unit 102a will be described in detail. The description of the leg unit 102a is to be understood in such a way that it is transferable to the additional leg unit 104a. It is also conceivable that an additional leg unit is implemented mirror-symmetrically to the leg unit. It is in particular conceivable that a leg unit and an additional leg unit are respectively embodied as a right leg unit and a left leg unit, or vice versa.

In the case that is shown here the person 200a wears the leg unit 102a on a right leg 204a. The leg unit 102a is arranged on a rear side 211a of the leg 204a of the person 200a. Furthermore the person 200a wears the additional leg unit 104a on a left leg 206a. It is also conceivable that a person wears a leg unit on a left leg and wears an additional leg unit on a right leg. It is further conceivable for a person to wear only one leg unit. Moreover it is conceivable that a wearable sitting-posture assisting device comprises only one leg unit. It is also conceivable that a leg unit is arranged sideways on a leg and/or on a front side of a leg and/or between two legs of a person.

The person 200a is sitting or partly sitting on the wearable sitting-posture assisting device 100a in a sitting direction 134a. If the person 200a faces forward, he faces in the sitting direction 134a and/or looks in the sitting direction 134a. The sitting direction 134a is oriented parallel to a ground above which the person 200a is sitting or on which the person 200a is walking or standing.

The leg unit 102a comprises an upper leg part 106a. The upper leg part 106a comprises an upper leg support 108a. The upper leg part 106a comprises an upper longitudinal leg axis 110a. The upper longitudinal leg axis 110a is oriented orthogonally to the sitting direction 134a. The upper leg support 108a has a main extension direction that is oriented parallel to the upper longitudinal leg axis 110a. The upper longitudinal leg axis 110a is oriented parallel to a main extension direction of a thigh 208a of the leg 204a of the person 200a, in particular when the person 200a is sitting and/or partly sitting and/or walking and/or getting up and/or standing while wearing the wearable sitting-posture assisting device 100a.

The upper leg part 106a comprises a seat unit 112a. The seat unit 112a is connected with the upper leg support 108a. In the partial sitting posture and/or in the sitting posture the person 200a sits on the seat unit 112a. In the case shown the person 200a is sitting in the partial sitting posture on the seat unit 112a and on a seat unit 114a of the additional leg unit 104a. The seat unit 112a comprises a seat element 116a. The seat element 116a contacts the thigh 208a of the person 200a. In the sitting posture and/or in the partial sitting posture the seat element 116a contacts a buttock 210a of the person 200a. The seat unit 112a comprises a sitting surface 118a. The seat element 116a comprises the sitting surface 118a. The sitting surface 118a is configured to enable the person 200a to sit down on the sitting surface 118a with his thigh 208a and/or with his buttock 210a. A shape of the sitting surface 118a is at least partially adapted to the thigh 208a and/or the buttock 210a of the person 200a. The sitting surface 118a is curved. The sitting surface 118a is concavely curved and/or bent.

It is also conceivable that a wearable sitting-posture assisting device comprises only one seat unit, in particular a shared seat unit of two leg units. In that case it is in particular conceivable for the seat unit to be saddle-shaped and/or formed like a saddle and/or in particular to be arranged between a person's legs.

For a connection to the thigh 208a of the person 200a the upper leg part 106a comprises a thigh connection unit 120a. The thigh connection unit 120a is connected with the upper leg support 108a. The thigh connection unit 120a is configured to connect the upper leg part 106a with the thigh 208a of the person 200a. The thigh connection unit 120a comprises a thigh strap 122a. The thigh strap 122a is fixated on the thigh 208a of the person 200a.

The wearable sitting-posture assisting device 100a comprises a lower leg part 124a. The lower leg part 124a comprises a lower leg support 126a. The lower leg part 124a comprises a lower longitudinal leg axis 128a. The lower longitudinal leg axis 128a is oriented orthogonally to the sitting direction 134a. The lower longitudinal leg axis 128a and the upper longitudinal leg axis 110a are arranged in a shared plane. The lower leg support 126a has a main extension direction that is oriented parallel to the lower longitudinal leg axis 128a. The lower longitudinal leg axis 128a is oriented parallel to a main extension direction of a shank 212a of the leg 204a of the person 200a, in particular if the person 200a is sitting and/or partly sitting and/or walking and/or standing while wearing the wearable sitting-posture assisting device 100a.

The upper leg part 106a and the lower leg part 124a define a sitting angle 130a. The sitting angle 130a is an angle spanned by the upper longitudinal leg axis 110a and the lower longitudinal leg axis 128a. The sitting angle 130a is similar or identical to an angle between the thigh 208a and the shank 212a of the person 200a. The sitting angle 130a having a value between 60° and 130°, in particular a value of at least substantially 90°, corresponds to different sitting postures or at least one sitting posture. The sitting angle 130a having a value between 130° and 170° corresponds to different partial sitting postures. If the person 200a is standing while wearing the wearable sitting-posture assisting device 100a, the sitting angle 130a presents a value between 160° and 180°, in particular a value of at least substantially 180°. If the person 200a is walking while wearing the wearable sitting-posture assisting device 100a, the sitting angle 130a may be clearly different from 180°, in particular if the person 200a bends his knee 202a. The sitting angle 130a and an analogously defined additional sitting angle of the additional leg unit 104a are advantageously identical in the sitting posture and/or in the partial sitting posture and/or when standing. It is however also conceivable that the person 200a is sitting on the wearable sitting-posture assisting device 100a in a sitting posture or partial sitting posture with the sitting angle 130a and the additional sitting angle differing from each other, in particular by up to 5°, by up to 10°, by up to 15°, by up to 20°, by up to 30°, by up to 40° or even more. When the person 200a walks while wearing the wearable sitting-posture assisting device 100a, the sitting angle 130a and the additional sitting angle may be clearly different from each other, for example when the person 200a is bending his knees in respectively different ways.

The leg unit 102a comprises a knee joint 131a, which pivotally connects the upper leg part 106a with the lower leg part 124a. The knee joint 131a connects the upper leg part 106a with the lower leg part 124a pivotally around a knee joint axis 132a. The knee joint axis 132a is oriented orthogonally to the upper longitudinal leg axis 110a. The knee joint axis 132a is oriented orthogonally to the lower leg axis 128a. The knee joint axis 132a is oriented orthogonally to the sitting direction 134a. The knee joint 131a is implemented partly integrally with the upper leg support 108a. The knee joint 131a is implemented partly integrally with the lower leg support 126a. The knee joint 131a comprises at least one bearing 136a that connects the upper leg support 108a with the lower leg support 126a.

The leg unit 102a comprises a blocking unit 138a, which is configured for a blocking of the knee joint 131a. The blocking unit 138a is configured to restrict the sitting angle 130a to a minimum value. The blocking unit 138a is configured to allow the person 200a to select the minimum value of the sitting angle 130a. When the blocking unit 138a is in the blocked state, this allows the person 200a sitting down on the wearable sitting-posture assisting device 100a with the minimum value of the sitting angle 130a. The blocking unit 138a is configured to be operated by the person 200a. The blocking unit 138a comprises a blocking element 140a. The blocking element 140a is embodied as a spring, in particular a gas compression spring. The blocking element 140a is configured to be blocked to different lengths. The blocking element 140a is connected with the upper leg support 108a. The blocking element 140a is connected with the lower leg support 126a. The blocking element 140a is configured for damping a movement of the upper leg part 106a relative to the lower leg part 124a, in particular when the person 200a is sitting down.

The leg unit 102a comprises a ground contact unit 152a. The ground contact unit 152a is connected with a foot unit 142a. The ground contact unit 152a is connected with the lower leg support 126a. The ground contact unit 152a comprises a ground contact element 154a. When the person 200a is sitting or partly sitting on the wearable sitting-posture assisting device 100a, the ground contact unit 152a, in particular the ground contact element 154a, is in contact with the ground. The ground contact unit 152a, in particular the ground contact element 154a, is configured to transfer a portion of the weight force of the person 200a into the ground. The ground contact element 154a is rounded. The ground contact element 154a is implemented like a sphere. The ground contact element 154a is made of rubber. However, other than the above-mentioned shapes and/or materials are also conceivable for the ground contact element.

When the person 200a is sitting or partly sitting on the wearable sitting-posture assisting device 100a, the weight force of the person 200a is transferred at least partially, in particular indirectly or directly, from the seat unit 112a to the upper leg support 108a, from the upper leg support 108a to the knee joint 131a, from the knee joint 131a to the lower leg support 126a, from the lower leg support 126a to the ground contact element 154a and from the ground contact element 154a to the ground.

In particular, the weight force of the person 200a is additionally transferred to the ground via the foot and/or via a shoe 214a of the person 200a. The ground contact element 154a is preferentially arranged on a rear side of the shoe 214a of the person 200a. When the person 200a is sitting or part sitting on the wearable sitting-posture assisting device 100a, the foot and/or the shoe 214a of the person 200a is in contact with the ground in addition to the ground contact element 154a. Preferably the ground contact element 154a is arranged to be free of contact with the ground when the person is walking and/or standing while wearing the wearable sitting-posture assisting device 100a.

The wearable sitting-posture assisting device 100a comprises an upper body wearing unit 156a. The person 200a wears the upper body wearing unit 156a on his upper body 216a, wherein the upper body 216a may comprise hips and/or a waist of the person 200a. The upper body wearing unit 156a comprises a belt 158a. The upper body wearing unit 156a further comprises suspenders 160a, 162a. The leg unit 102a is connected with the upper body wearing unit 156a. The additional leg unit 104a is connected with the upper body wearing unit 156a. It is conceivable for the upper body wearing unit to comprise only suspenders and no belt, or vice versa. It is also conceivable that a wearable sitting-posture assisting device 100a is connected only with the legs and/or with the feet and/or with the shoes of a person who it is worn by.

The leg unit 102a comprises a foot unit 142a. The foot unit 142a is configured for a connection to a shoe 214a and/or a foot of the person 200a. The foot unit 142a comprises a shoe connector 144a for a connection to the shoe 214a and/or the foot of the person 200a. The shoe connector 144a comprises a strap 146a that is fixated on the shoe 214a of the person 200a. The foot unit 142a is connected with an end section 36a of the leg unit 102a. The foot unit 142a is supported in such a way that it pivotable around the lower longitudinal leg axis 128a relative to the leg unit 102a. The foot unit 142a comprises a foot unit support 148a. The foot unit support 148a is connected with the lower leg part 124a. The foot unit support 148a comprises a bracket 150a. The bracket 150a is supported in such a way that it is rotatable around a rotation axis along its main extension direction. The bracket 150a is rotatable around the rotation axis relative to the leg unit 102a. The foot unit 142a further comprises a shoe adapter 143a. The shoe adapter 143a is at least indirectly connected with the foot unit support 148a. The shoe adapter 143a is couplable with the shoe connector 144a. The shoe connector 144a is couplable with the leg unit 102a via the shoe adapter 143a.

FIGS. 4 and 5 show the foot unit 142a in a schematic side view and a perspective interior view. The wearable sitting-posture assisting device 100a comprises at least one bearing unit 12a. The wearable sitting-posture assisting device 100a comprises a bearing unit 12a for each leg unit 102a, 104a (see FIGS. 2 and 3). In the present case the wearable sitting-posture assisting device 100a comprises two bearing units 12a. The bearing units 12a are implemented to be at least substantially identical to each other. Furthermore the bearing units 12a are implemented and/or arranged mirror-symmetrically to each other. For the sake of a better overview, only one bearing unit 12a is described and given a reference numeral in the figures and in the description, in particular using the bearing unit 12a as an example, which is configured to be arranged on a right foot and/or shoe 214a of the person 200a. The description may be respectively transferred to further bearing units 12a. In the following the bearing unit 12a, which interacts with the leg unit 102a, is described in detail.

The bearing unit 12a is arranged on an end section 36a of the leg unit 102a. The end section 36a extends from a free open end of the leg unit 102a in a direction of the leg unit 102a over a length of maximally 15% of a main extension of the leg unit 102a. The bearing unit 12a is in the present case arranged on the end section 38a of the lower leg part 124a of the leg unit 102a. Furthermore the bearing unit 12a is arranged at the ground contact unit 152a. The foot unit 142a and/or the ground contact unit 152a are/is arranged on the end section 36a of the leg unit 102a, in particular of the lower leg part 124a of the leg unit 102a. The foot unit support 148a forms a housing which the bearing unit 12a is arranged in at least partly, preferably to a large extent and particularly preferably completely.

The bearing unit 2a movably supports at least a portion of the foot unit 142a. The bearing unit 12a supports at least a portion of the foot unit 142a in such a way that it is translationally movable at least transversely to the upper longitudinal leg axis 110a and/or to the lower longitudinal leg axis 128a. The bearing unit 12a supports at least a portion of the foot unit 142a in such a way that it is translationally movable at least substantially orthogonally to the upper longitudinal leg axis 110a and/or to the lower longitudinal leg axis 128a. The translational support is in the present case equivalent to a straight-line support. The bearing unit 12a furthermore supports a portion of the foot unit 142a in such a way that it is translationally movable at least substantially parallel to the leg bending plane 16a. In an angled state, the leg unit 102a herein defines the leg bending plane 16a. In the present case the bearing unit 12a supports at least the portion of the foot unit 142a exclusively parallel to the leg bending plane 16a. The portion of the foot unit 142a is displaceable relative to the leg unit 102a by means of the bearing unit 12a The portion of the foot unit 142a is in the present case displaceable relative to the leg unit 102a by at least 5 cm. In the present case the bearing unit 12a supports, constituting the portion of the foot unit 142a, the shoe adapter 143a and/or the shoe connector 144a relative to one another. Alternatively or additionally a bearing unit could support the foot unit at least partly translationally at least substantially orthogonally to the leg bending plane.

FIGS. 6 and 7 show a portion of the bearing unit 12a in schematic perspective views. The bearing unit 12a is in the present case embodied as a slide bearing. The bearing unit 12a comprises at least one bearing element 32a. The bearing element 32a is connected with the foot unit 142a. The bearing element 32a is arranged in the housing formed by the foot unit support 148a. In the present case the bearing element 32a is connected, in particular screwed, with the foot unit support 148a. Alternatively or additionally the bearing element could be implemented at least partly integrally with the foot unit, in particular the foot unit support. Moreover the bearing element could be connected with the foot unit in another way that is deemed advantageous by someone skilled in the art. The bearing element 32a comprises a guide rail 33a. Alternatively the bearing element 32a may form the guide rail 33a.

For the realization of a bearing the bearing unit 12a comprises at least one further bearing element 34a. The further bearing element 34a is embodied correspondingly to the bearing element 32a. The further bearing element 34a is connected with the bearing element 32a. The bearing element 32a is at least displaceable relative to the further bearing element 34a. The further bearing element 34a comprises a further guide rail 35a. The further guide rail 35a is embodied correspondingly to the guide rail 33a. The bearing element 32a and the further bearing element 34a mutually guide each other. Alternatively or additionally a bearing unit could be embodied as a roller bearing, wherein in particular, to realize the roller bearing, the bearing unit may comprise at least one roller element, preferably a plurality of roller elements arranged between a bearing element and a further bearing element, which may be arranged between a bearing element and a further bearing element supporting said bearing elements in such a way that these roll on each other. Such a roller element could be embodied, for example, as a sphere, a roll or the like.

The bearing unit 12a is arranged on and/or connected with the shoe adapter 143a. In the present case the further bearing element 34a is arranged on and/or connected with the shoe adapter 143a. Alternatively a bearing unit could be arranged on and/or connected with another component of the wearable sitting-posture assisting device 100a, like for example a leg unit and/or a ground contact unit. In particular, a bearing unit could be arranged between the upper leg part and the lower leg part, for example in a proximity of a knee joint. Furthermore a bearing unit, at least one of the bearing elements, could also be arranged on the shoe connector.

The bearing element 32a and the further bearing element 34a are arranged in such a way that their main extension directions are oriented at least transversely, in particular at least substantially orthogonally, to the upper longitudinal leg axis 110a and/or the lower longitudinal leg axis 128a. Furthermore the bearing element 32a and the further bearing element 34a are arranged in such a way that their main extension directions are situated at least substantially parallel to the leg bending plane 16a.

At least in one bearing position, in particular in a first bearing position, the bearing element 32a and the further bearing element 34a are arranged at least partly within each other. In the present case the further bearing element 34a is arranged at least partially in the bearing element 32a. The further bearing element 34a is at least partially engaged around by the bearing element 32a. The further bearing element 34a engages around the bearing element 32a from at least two opposite-situated sides. Moreover the further bearing element 34a engages at least partly around the foot unit support 148a. Furthermore the bearing element 32a is engaged around by the foot unit support 148a.

For an expansion and/or contraction of the bearing unit 12a the bearing unit 12a comprises at least one telescopic pull-out 28a. The bearing element 32a and the further bearing element 34a form the telescopic pull-out 28a. Alternatively or additionally the bearing unit 12a could comprise a plurality of telescopic pull-outs 28a, which could in particular be arranged step-wise.

The bearing unit 12a has a first bearing position. In the first bearing position the bearing unit 12a is contracted. In the first bearing position the bearing unit 12a has a first main extension. For an expansion the further bearing element 34a of the bearing unit 12a can be pulled out along the bearing element 32a. The bearing unit 12a has a second bearing position. In the second bearing position the bearing unit 12a is fully expanded. In the second bearing position the bearing unit 12a has a second main extension. The second main extension is larger than the first main extension. In the present case the second main extension in the second bearing position of the bearing unit 12a is larger than the first main extension of the bearing unit 12a in the first bearing position by at least 25%. The second main extension of the bearing unit 12a in the second bearing position is at least substantially equivalent to the total sum of the main extensions of the individual bearing elements 32a, 34a of the bearing unit 12a. In the present case the bearing unit 12a is expandable in one direction only. The bearing unit 12a is at least partly expandable at least in an expansion direction 24a away from the leg unit 102a. In the present case the bearing unit 12a is contractible in one direction only. The bearing unit 12a is at least partly contractible at least in a contraction direction 26a towards the leg unit 102a. The expansion direction 24a and the contraction direction 26a are oriented counter to each other. The expansion direction 24a and the contraction direction 26a are oriented anti-parallel to each other.

The bearing unit 12a comprises at least one reset element 30a. The reset element 30a is configured, in a bearing position that differs from the first bearing position, to at least partially apply a reset force to the foot unit 142a. The reset force points in the direction of the contraction direction 26a. The reset element 30a is embodied as an elastic element. In the present case the reset element 30a is embodied as a spring. Alternatively a reset element could be embodied as a rubber strap or the like.

The reset element 30a is connected with the further bearing element 34a of the bearing unit 12a. Further the reset element 30a is connected with the foot unit support 148a. If the bearing element 32a and the further bearing element 34a are displaced out of the first bearing position of the bearing unit 12a, the reset element 30a applies the reset force to them relative to each other. Alternatively a reset element could be connected with a further component, for example with the ground contact unit, with a leg unit, or the like.

In at least one bearing position the reset element 30a of the bearing unit 12a is arranged such that it is partly overlapped. Viewed in a direction at least substantially orthogonally to the leg bending plane 16a, the reset element 30a is arranged such that it is overlapped. The reset element 30a is arranged at least partially within the bearing unit 12a. The reset element 30a is arranged within the further bearing element 34*a*. The further bearing element 34*a* comprises a recess. The reset element 30*a* is arranged in the recess.

The bearing unit 12*a* comprises at least one delimitation element 58*a*. The delimitation element 58*a* is configured to delimit a translational movement of the portion of the foot unit 142*a*. The delimitation element 58*a* forms an abutment for the bearing elements 32*a*, 34*a*. In the present case the delimitation element 58*a* is formed at least partially by the foot unit 142*a*. The delimitation element 58*a* is formed by the foot unit support 148*a*. Alternatively or additionally a delimitation element 58*a* could be realized at least partly integrally with at least one bearing element 32*a*, 34*a*.

The shoe adapter 143*a* and the shoe connector 144*a* are couplable with each other along a direction that extends transversely to the upper longitudinal leg axis 110*a* and/or to the lower longitudinal leg axis 128*a* by way of the shoe adapter 143*a* and the shoe connector 144*a* being guided on each other and/or within each other along the coupling direction 20*a*. Furthermore the shoe adapter 143*a* and the shoe connector 144*a* are couplable with each other along a coupling direction 20*a* at least substantially orthogonally to the leg bending plane 16*a*. In particular, the coupling direction 20*a* is oriented at least substantially orthogonally to the expansion direction 24*a* and/or to the contraction direction 26*a* of the bearing unit 12*a*. In the present case the shoe adapter 143*a* and the shoe connector 144*a* are couplable exclusively at least substantially orthogonally to the leg bending plane 16*a*. Alternatively or additionally a shoe adapter and a shoe connector could be couplable at least substantially parallel to the leg bending plane.

For a coupling of the shoe adapter 143*a* and the shoe connector 144*a* with each other, the wearable sitting-posture assisting device 100*a* comprises at least one quick coupling 38*a*. FIGS. 8 and 9 show the quick coupling 38*a* in schematic perspective views. By means of the quick coupling 38*a* the shoe adapter 143*a* and the shoe connector 144*a* are couplable with each other at least transversely to the upper longitudinal leg axis 110*a* and/or the lower longitudinal leg axis 128*a*. Furthermore the shoe adapter 143*a* and the shoe connector 144*a* are couplable with each other by the quick coupling 38*a* at least substantially orthogonally relative to the leg bending plane 16*a*. The quick coupling 38*a* is configured for coupling the shoe adapter 143*a* and the shoe connector 144*a* with each other without tools. The quick coupling 38*a* is configured for a repeated coupling of the shoe adapter 143*a* and the shoe connector 144*a*. The quick coupling 38*a* brings about a coupling of the shoe adapter 143*a* with the shoe connector 144*a* by means of just one movement of a leg and/or a foot of a person 200*a*.

For a realization of the quick coupling 38*a* different implementations of a coupling are conceivable, like for example by hook-and-loop fastener, magnetic lock, click closure and/or latch closure, twist lock and/or bayonet lock, or the like. In the present case the quick coupling 38*a* is realized at least partly as a magnet lock. Furthermore the quick coupling 38*a* is realized at least partly as a latch closure. The quick coupling 38*a* is thus realized as a combination of a magnetic lock and a latch closure.

For a coupling the quick coupling 38*a* comprises at least one quick coupling element 40*a*. Furthermore the quick coupling 38*a* comprises at least one further quick coupling element 42*a*. The further quick coupling element 42*a* is embodied correspondingly to the quick coupling element 40*a*.

The quick coupling 38*a* is arranged at least partially on the foot unit 142*a*. The quick coupling element is arranged on the shoe adapter 143*a*. The further quick coupling element 42*a* is arranged on the shoe connector 144*a*. It is conceivable for the quick coupling element to be implemented at least partly integrally with the foot unit, the shoe adapter and/or the bearing unit, in particular the bearing element. It is further conceivable for the further quick coupling element to be implemented at least partly integrally with the foot unit, the shoe connector and/or the bearing unit, in particular the further bearing element.

The quick coupling 38*a* is configured at least for a force-fit and/or form-fit coupling of the shoe adapter 143*a* and the shoe connector 144*a*. The quick coupling 38*a* comprises at least one latch element 44*a*. The latch element 44*a* is configured at least partly to implement a coupling of the shoe adapter 143*a* with the shoe connector 144*a*. The latch element 44*a* is at least partly elastically deformable. The latch element 44*a* is configured at least for an implementation of a latch connection, for example by a force-fit and/or form-fit connection. The latch element 44*a* is configured to be at least partly deflected and/or deformed when a coupling is established. The latch element 44*a* has a protrusion that is, for example, conus-shaped. The quick coupling 38*a* further comprises at least one further latch element 46*a*. The further latch element 46*a* is embodied correspondingly to the latch element 44*a*. In a coupling the further latch element 46*a* engages behind the latch element 44*a*, in particular the protrusion of the latch element 44*a*, as a result of which the latch elements 44*a*, 46*a* latch with each other. In the present case the quick coupling element 40*a* comprises the latch element 44*a*. Furthermore the further quick coupling element 42*a* comprises the further latch element 46*a*. Alternatively the quick coupling element could form the latch element at least partly integrally and/or the further quick coupling element could form the further latch element at least partly integrally.

The quick coupling 38*a* comprises at least one magnet element 48*a*. The magnet element 48*a* is configured at least partially to bring about a coupling of the shoe adapter 143*a* with the shoe connector 44*a*. The magnet element 48*a* is embodied to be permanent magnetic. Alternatively the magnet element 48*a* could also be embodied to be magnetizable. The magnet element 48*a* is made at least partially of a ferromagnetic material. The magnet element 48*a* is made at least partially of a hard magnetic material. The magnet element 48*a* is made at least partially of iron, nickel, cobalt or the like. Furthermore the quick coupling 38*a* comprises at least one further magnet element 50*a*. The further magnet element 50*a* is embodied correspondingly to the magnet element 48*a*. The further magnet element 50*a* is magnetizable. The further magnet element 50*a* is made at least partially of a ferromagnetic material. The further magnet element 50*a* is made at least partially of a soft magnetic material. The further magnet element 50*a* is made at least partially of iron, nickel, cobalt or the like. In a coupling the magnet element 48*a* and the further magnet element 50*a* interact with each other to generate a magnetic attracting force. By an interaction of the magnet element 48*a* and the further magnet element 50*a* at least the shoe adapter 143*a* and the shoe connector 144*a* are movable towards each other at least transversely to the upper longitudinal leg axis 110*a* and/or the lower longitudinal leg axis 128*a*. In the present case the quick coupling element 40*a* comprises the magnet element 48*a*. Furthermore the further quick coupling element 42*a* comprises the further magnet element 50*a*. Alternatively the quick coupling element could implement the magnet element at least partly integrally and/or the further quick coupling element could implement the further magnet element at least partly integrally. The magnet element could also be implemented at least partly integrally with the latch element and/or the further magnet element could be implemented at least partly integrally with the further latch element.

The magnet element 48a initiates a coupling of the shoe adapter 143a with the shoe connector 144a by means of the latch element 44a. By the interaction between the magnet element 48a and the further magnet element 50a, the latch element 44a and the further latch element 46a are moved towards each other. The latch element 44a is deflected by the further latch element 46a. The latch element 44a latches with the further latch element 46a. In the coupled state of the shoe adapter 143a with the shoe connector 144a the coupling is established at least partly by a force-fit and/or form-fit latch connection. Alternatively or additionally the coupling could be brought about at least partly by a magnetic force-fit connection due to the interaction between the magnet element and the further magnet element.

Furthermore, in a coupled state, the quick coupling 38a supports the shoe adapter 143a and the shoe connector 144a around a rotation axis 52a at least transversely to the upper longitudinal leg axis 110a and/or the lower longitudinal leg axis 128a. The rotation axis 52a is oriented at least substantially orthogonally to the upper longitudinal leg axis 110a and/or the lower longitudinal leg axis 128a. The rotation axis 52a is further oriented at least substantially orthogonally to the leg bending plane 16a. The quick coupling 38a comprises at least one axle 60a. The quick coupling 38a further comprises at least one axle accommodation 62a. The axle accommodation 62a is embodied correspondingly to the axle 60a. In a coupled state the axle 60a is arranged at least partially in the axle accommodation 62a. The rotation axis 52a is defined at least partially by the main extension direction of the axle 60a and/or of the axle accommodation 62a. In the present case the quick coupling element 40a comprises the axle 60a. In the present case the further quick coupling element 42a comprises the axle accommodation 62a.

For a decoupling of the shoe adapter 143a and the shoe connector 144a, the wearable sitting-posture assisting device 100a comprises at least one quick release unit 54a. The quick release unit 4a is configured for a mechanical decoupling of the coupling. Alternatively a decoupling could also be effected electronically.

The wearable sitting-posture assisting device 100a comprises at least one quick release unit 54a, which is configured to release the shoe adapter 143a and the shoe connector 144a from each other without a tool. The quick release unit 54a is configured to release a coupling of the shoe adapter 143a and the shoe connector 144a established by the quick coupling 38a in a tool-less, non-destructive and/or repeatable manner. Furthermore the coupling can be decoupled in a one-handed, one-legged and/or one-footed manner, advantageously with one single movement of a hand, a foot and/or a leg of the person 200a. The quick release unit 54a is configured to undo a latching of the latch elements 44a, 46a and/or to space the magnet elements 48a, 50a apart from each other such that their mutual magnetic attracting forces substantially disappear.

For a decoupling the quick release unit 54a comprises at least one actuation element 56a. The actuation element 56a is in the present case embodied as a bracket. Alternatively an actuation element could also be embodied as an operating lever, an operating button and/or an operating bolt. For an actuation of the quick release unit 54a the actuation element 56a is movable relative to the shoe adapter 143a and/or to the shoe connector 144a. The actuation element 56a is operable at least substantially parallel to the upper longitudinal leg axis 110a and/or the lower longitudinal leg axis 128a. The actuation element 56a can be pulled out.

In an actuation the actuation element 56a at least indirectly displaces the latch element 44a relative to the magnet element 48a. In the present case the actuation element 56a displaces the latch element 44a directly. Alternatively a quick release unit may comprise at least one transfer mechanism that is configured, during an actuation of the actuation element, to displace the latch element relative to the magnet element. By the actuation the further latch element 46a is displaced and/or deformed, as a result of which the latch element 44a and the further latch element 46a unlatch from each other. Furthermore the magnet element 48a is displaceable relative to the further magnet element 50a by the actuation element 56a, as a result of which a magnetic interaction of the magnet elements 48a, 50a is interrupted.

FIG. 10 shows a schematic flow chart of a method for an operation of the wearable sitting-posture assisting device 100a.

The method comprises at least one method step 300a. In the method step 300a a foot and/or a shoe 214a of a person 200a is connected with the shoe connector 144a.

The method comprises at least one further method step 302a. In the further method step 302a the shoe adapter 143a and the shoe connector 144a are coupled with each other at least transversely to the upper longitudinal leg axis 110a and/or the lower longitudinal leg axis 128a of the leg unit 102a, wherein the quick coupling 38a couples the shoe adapter 143a and the shoe connector 144a with each other without tools, wherein the at least one latch element 4a of the quick coupling 38a at least partially realizes the coupling of the shoe adapter 143a with the shoe connector 144a. For this purpose the shoe connector 144a is moved into a proximity of the shoe adapter 143a by the person 200a wearing the shoe connector 144a by means of the foot. The magnet element 48a interacts with the further magnet element 50a. A resulting magnetic force moves the shoe connector 144a and the shoe adapter 143a towards each other. A coupling of the shoe adapter 143a and the shoe connector 144a is initiated.

The method comprises at least one further method step 304a. In the further method step 304a the latch element 44a is latched with the further latch element 46a by the attracting force generated by the magnet element 48a, 50a. A coupling of the shoe connector 144a with the shoe adapter 143a is induced. The coupling is effected at least partly, in particular to a large extent and particularly preferably completely via a latching of the latch elements 44a, 46a. Alternatively or additionally the coupling may be effected at least partly magnetically.

The method comprises a further method step 306a. In the further method step 306a free locomotion is enabled for a person 200a wearing the wearable sitting-posture assisting device 100a. At least the portion of the foot unit 142a that is configured for a connection of a shoe 214a and/or a foot of the person 200a, in particular the shoe adapter 143a and the shoe connector 14a, is translationally moved transversely to the upper longitudinal leg axis 110a and/or the lower longitudinal leg axis 128a. The movement is enabled by the bearing unit 12a. Alternatively or additionally a movement of a portion of the foot unit 142a transversely to the upper longitudinal leg axis 110a and/or the lower longitudinal leg axis 128a may also be effected in a state when sitting, for example for changing a sitting posture.

The method comprises at least one further method step 308a. In the further method step 308a a coupling between the shoe adapter 143a and the shoe connection 144a is undone. The quick release unit 54a releases the coupling. The person 200a actuates the actuation element 56a. The actuation element 56a is actuated by one-handed pulling-out. The actuation element 56a initiates a decoupling. The actuation element 56a displaces the latch elements 44a, 46a relative to each other. The actuation element 56a unatches the latch elements 44a, 46a from each other. The actuation element 56a further displaces the magnet elements 48a, 50a relative to each other, which results in their interaction being at least substantially negligible. The shoe adapter 143a and the shoe connector 144a are decoupled from each other.

In regard to further method steps of the method for an operation of the wearable sitting-posture assisting device 100a the above description of the wearable sitting-posture assisting device 100a may be referred to as this description is to be read analogously also onto the method and thus all features relating to the wearable sitting-posture assisting device 100a shall be considered to be disclosed for the method for the operation of the wearable sitting-posture assisting device 100a as well.

In FIGS. 11 to 13 a further exemplary embodiment of the invention is shown. The following description and the drawings are substantially limited to the differences between the exemplary embodiments, wherein regarding structural components having the same designation, in particular regarding structural components having the same reference numerals, the drawings and/or the description of the other exemplary embodiment of FIGS. 1 to 10 may principally be referred to as well. To distinguish between the exemplary embodiments, the letter a has been added to the reference numerals of the exemplary embodiments of FIGS. 1 to 10. In the exemplary embodiment of FIGS. 11 to 13 the letter a has been substituted by the letter b.

FIG. 11 shows a portion of an alternative wearable sitting-posture assisting device 100b in a schematic view. A foot unit 142b, a bearing unit 12b and a portion of a leg unit 102b of the wearable sitting-posture assisting device 100b are illustrated. The foot unit 142b comprises at least one at least partially rubber-elastic joint unit 218b, which is in particular formed at least partially of an elastomer, for a connection to the leg unit 102b. The wearable sitting-posture assisting device 100b in particular comprises a further foot unit, a further bearing unit, a further joint unit and a further leg unit, which are not shown here for the sake of a better overview. The following description of the foot unit 142b, the bearing unit 12b, the joint unit 218b and the leg unit 102b is in particular analogously transferable to the further foot unit, the further bearing unit, the further joint unit and the further leg unit. The joint unit 218b comprises at least one joint base body 224b, which is implemented to be rubber-elastic. The joint unit 218b, in particular the joint base body 224b, is implemented to be deformable differently than plastically deformable, in particular elastically deformable, by forces acting onto the joint unit 218b, in particular onto the joint base body 224b, during a use of the wearable sitting-posture assisting device 100b. The joint unit 218b, in particular the joint base body 224b, is connected with at least one further portion of the foot unit 142b, in particular with a foot unit support 148b of the foot unit 142b, and/or with the bearing unit 12b, in particular in a form-fit and/or force-fit manner. The joint base body 224b is embodied as an at least substantially L-shaped, respectively C-shaped, structural component. Alternatively other shapings of the joint base body 224b which are deemed expedient by someone skilled in the art are also conceivable. The leg unit 102b, in particular a lower leg support 126b of the leg unit 102b, extends through the joint unit 218b, in particular through a pass-through 226b in the joint base body 224b. The leg unit 102b, in particular the lower leg support 126b, is coupled with the joint unit 218b, in particular indirectly via at least one coupling element 222b of the foot unit 142b. The joint base body 224b is made of an elastomer, in particular a rubber. Alternatively it is conceivable for the joint base body 224b to be made of a material different than an elastomer and in particular to comprise at least one rubber-elastic and/or shock-absorbing component, like for example a spring element, a pneumatic damper, a hydraulic damper, a shape-memory metal, or the like.

The joint unit 218b, in particular the joint base body 224b, is implemented to be rotationally and/or translationally elastically deformable. In the present exemplary embodiment the joint unit 218b, in particular the joint base body 224b, is exemplarily implemented such that it is rotationally and translationally elastically deformable. The joint base body 224b is implemented such that it is elastically deformable rotationally around a first rotation axis 228b that extends at least substantially parallel to a contraction direction 26b of the bearing unit 12b. A rotation of a foot that is connected with the foot unit 142b around the first rotation axis 228b at least substantially corresponds to a pronation, respectively a supination, of the foot (not shown here in detail). The joint base body 224b is implemented such that it is elastically deformable rotationally around a second rotation axis 230b that extends at least substantially orthogonally to a longitudinal leg axis, in particular a lower longitudinal leg axis 128b. A rotation of a foot that is connected with the foot unit 142b around the second rotation axis 230b at least substantially corresponds to a flection, respectively an extension, of the foot. The joint base body 224b is implemented to be elastically deformable rotationally around a third rotation axis 232b that extends at least substantially parallel to the longitudinal leg axis, in particular the lower longitudinal leg axis 128b. The joint base body 224b is implemented to be elastically deformable translationally along any movement axes, in particular at least substantially orthogonally and/or at least substantially parallel to the rotation axes 228b, 230b, 232b. The joint base body 224b is configured for a damping, in particular by a rubber-elasticity of the joint base body 224b, of oscillations occurring during a use of the wearable sitting-posture assisting device 100b, in particular while a user is walking with the wearable sitting-posture assisting device 100b. In particular, the joint unit 218b, in particular the joint base body 22b, is implemented to be rubber-elastic such that the joint unit 218b, in particular the joint base body 22b, is deformable, in particular translationally deformable, under a load of maximally 100 Newton, preferably no more than 70 Newton, particularly preferably no more than 50 Newton and very particularly preferably maximally 30 Newton, by a maximum extent between 0.1 cm and 7 cm, preferentially between 0.1 cm and 5 cm, especially preferentially between 0.1 cm and 3 cm and very especially preferentially between 0.1 cm and 2 cm, relative to a basic shape in a load-free state of the joint unit 218b. In particular, the joint unit 218b, in particular the joint base body 224b, is implemented to be rubber-elastic such that the joint unit 218b, in particular the joint base body 22b, is rotationally deformable, under a load of maximally 100 Newton, preferably no more than 70 Newton, particularly preferably no more than 50 Newton and very particularly preferably maximally 30 Newton, by a maximum rotation angle between 5° and 60°, preferably between 5° and 45°, particularly preferably between 5° and 30° and very particularly preferably between 5° and 20° relative to the basic shape.

The foot unit 142b comprises at least one coupling element 222b which is connected with the joint unit 218b, through which the leg unit 102b extends at least section-wise and which has material properties differing from the joint unit 218b, in particular has a harder material than the joint unit 218b. The coupling element 222b is embodied as a coupling sleeve. The coupling element 222b is connected with the joint base body 224b. The coupling element 222b is arranged in the joint base body 224b at the pass-through 226b and in particular extends through the pass-through 226b in the joint base body 224b. The coupling element 222b is made of a harder material than the joint base body 224b. The coupling element 222b has a lower elasticity than the joint base body 224b. The coupling element 222b is implemented to be at least substantially non-deformable, in particular to be deformable by a maximum extent of no more than 1 mm relative to a load-free basic shape of the coupling element 222b, by forces, in particular a force of maximally 100 N, acting onto the coupling element 222b during a use of the wearable sitting-posture assisting device 100b. The coupling element 222b is made of a synthetic material, in particular a thermoset material. Alternatively it is conceivable for the coupling element 222b to be made of a metal, of a composite material or of another material that is deemed expedient by someone skilled in the art. The coupling element 222b is made of a material that differs from an elastomer, in particular from a rubber. The joint base body 224b, which is in particular made of an elastomer, is connected with the coupling element 222b at least by substance-to-substance bond, in particular by vulcanization. Alternatively it is conceivable that the joint base body 224b is connected with the coupling element 222b by gluing, by latching, by pressing, or by another connection type that is deemed expedient by someone skilled in the art. The coupling element 222b is configured for a coupling with the leg unit 102b, in particular with the lower leg support 126b which extends through the coupling element 222b. The coupling element 222b comprises at least one coupling projection 234b, in particular a coupling pin, for a coupling with the lower leg support 126b. The coupling projection 234b extends into the pass-through 226b that is delimited by the coupling element 222b, respectively by the joint base body 224b. The coupling projection 234b is configured to enable a movement of the leg unit 102b, in particular of the lower leg support 126b, relative to the foot unit 142b, in particular to the joint base body 224b.

The coupling element 222b is embodied as a poka-yoke element. The coupling element 222b comprises orientation projections 236b, 238b arranged along a circumferential direction. An uneven number of orientation projections 238b, in particular one single orientation projection 238b, is implemented differently than remaining orientation projections 236b. In the present exemplary embodiment the coupling element 222b exemplarily comprises one single orientation projection 238b that is embodied differently than seven remaining orientation projections 236b. The coupling element 222b has, in particular along the circumferential direction, a flower-like shape, wherein in particular the orientation projections 236b, 238b correspond to imaginary petals of a flower. The, in particular flower-like, shaping of the coupling element 222b, in particular the orientation projections 236b, 238b, forms/form a rotationally fixed securing of the coupling element 222b relative to the joint unit 218b, in particular the joint base body 224b. The orientation projections 236b, 238b have an organic shape. The orientation projections 236b, 238b are implemented to be free of sharp edges and/or corners, in particular to be rounded. By this shaping the coupling element 222b, in particular the orientation projections 236b, 238b, is/are configured to keep tensioning between the coupling element 222b and the joint unit 218b, in particular the joint base body 224b, at a low level.

FIG. 12 shows a portion of the wearable sitting-posture assisting device 100b of FIG. 11 in a further schematic view. A connection region 240b between the joint unit 218b and a portion of the foot unit 142b and/or the bearing unit 12b is illustrated. The foot unit 142b comprises at least one buffer element 220b, which is configured for an impact-damping of an, in particular contracting, portion of the foot unit 142b, which a reset force has been applied to, and/or the bearing unit 12b. The foot unit 142b comprises a plurality of buffer elements 220b. The foot unit 142b comprises at least two buffer elements 220b, which are arranged, in particular on the joint base body 224b, such that they are spaced apart from one another, in particular along a direction extending at least substantially orthogonally to the contraction direction 26. In the present exemplary embodiment the foot unit 142b exemplarily comprises precisely two buffer elements 220b. The buffer elements 220b are implemented to be connected with the joint unit 218b, in particular connected integrally with the joint base body 224b. The buffer elements 220b are implemented to be rubber-elastic. The buffer elements 220b are made of the same material as the joint base body 224b, in particular of an elastomer. Alternatively it is conceivable that the buffer elements 220b are made of a material different than the joint base body 224b. The buffer elements 220b are arranged in the connection region 240b of the joint base body 224b with a portion of the foot unit 142b, in particular with the foot unit support 148b, and/or with the bearing unit 12b. In a first bearing position of the foot unit 142b the buffer elements 220b serve as an end abutment of a further bearing element 34b of the bearing unit 12b. The buffer elements 220b are configured to damp an impact of the further bearing element 34b, to which a reset force has been applied by a reset element 30b of the bearing unit 12b and which is in particular accelerated along the contraction direction 26b, onto the joint base body 224b. The buffer elements 220b have shock-absorbing characteristics. The buffer elements 220b are implemented to be elastically deformable by a force acting onto the buffer elements 220b due to the impact of the further bearing element 34b.

FIG. 13 shows a portion of the wearable sitting-posture assisting device 100b of FIG. 11 in a schematic sectional view. The joint unit 218b as well as a portion of the foot unit 142b and a portion of the bearing unit 12b are illustrated. The joint unit 218b is clearance-free connected, in particular pressed, with at least one portion of the foot unit 142b and/or of the bearing unit 12b. The joint unit 218b, in particular the joint base body 224b, is connected with at least one portion of the foot unit 142b and/or of the bearing unit 12b in a form-fit manner. The joint unit 218b, in particular the joint base body 224b, is clearance-free connected, in particular pressed, with a bearing element 32b and/or with a guide rail of the bearing unit 12b. In the present exemplary embodiment the joint unit 218b, in particular the joint base body 224b, is exemplarily clearance-free connected, in particular pressed, with the bearing element 32b of the bearing unit 12b. Alternatively or additionally it is conceivable that the joint unit 218b, in particular the joint base body 224b, is clearance-free connected, in particular pressed, with at least one portion of the foot unit 142b, in particular with the foot unit support 148*b*. The bearing element 32*b* and/or the guide rail, in the present exemplary embodiment in particular the bearing element 32*b*, are/is pressed into the joint base body 224*b*, in particular in a receiving opening 242*b* that is delimited by the joint base body 224*b*. The bearing element 32*b* and/or the guide rail, in the present exemplary embodiment in particular the bearing element 32*b*, have/has at least section-wise, in particular at least in a section extending within the joint base body 224*b*, a fir-tree geometry, in particular for the purpose of establishing a compression connection with the joint base body 224*b*. The bearing element 32*b* and/or the guide rail, in the present exemplary embodiment in particular the bearing element 32*b*, comprise/s on the section extending within the joint base body 224*b* projections 244*b*, in particular rib-like projections 244*b*, for the purpose of establishing a clearance-free, in particular rotationally fixed, connection with the joint base body 224*b*. The projections 244*b* implement the fir-tree geometry of the bearing element 32*b* and/or of the guide rail, in the present exemplary embodiment in particular of the bearing element 32*b*. The projections 244*b* are arranged in poka-yoke fashion, in particular for a realization of a predetermined orientation of the bearing unit 12*b* relative to the joint unit 218*b*, in particular the joint base body 224*b*.

The invention claimed is:

1. A wearable sitting-posture assisting device with at least one leg unit that defines at least one longitudinal leg axis and with at least one foot unit that is configured for a connection of a shoe and/or a foot of a person, wherein the foot unit comprises at least one shoe adapter and at least one shoe connector, which are couplable with one another at least transversely to the at least one longitudinal leg axis, comprising a quick coupling which is configured for a tool-less coupling of the shoe adapter and the shoe connector with each other, wherein the quick coupling comprises at least one latch element that is configured at least partially to create a coupling of the shoe adapter with the shoe connector.

2. The wearable sitting-posture assisting device according to claim 1, wherein the leg unit defines at least one leg bending plane, relative to which the shoe adapter and the shoe connector are couplable at least substantially orthogonally.

3. The wearable sitting-posture assisting device according to claim 1, wherein the quick coupling is configured at least for a force-fit and/or form-fit coupling of the shoe adapter and the shoe connector.

4. The wearable sitting-posture assisting device according to claim 1, wherein the quick coupling comprises at least one magnet element, which is configured at least for an initiation of a coupling of the shoe adapter with the shoe connector.

5. The wearable sitting-posture assisting device according to claim 4, wherein the magnet element is configured for activating a coupling of the shoe adapter with the shoe connector via the latch element.

6. The wearable sitting-posture assisting device according to claim 1, wherein the quick coupling supports the shoe adapter and the shoe connector rotatably around a rotation axis transversely to the at least one longitudinal leg axis.

7. The wearable sitting-posture assisting device according to claim 1, further comprising at least one quick release unit, which is configured to release the shoe adapter and the shoe connector from each other without a tool.

8. The wearable sitting-posture assisting device according to claim 7, wherein the quick release unit comprises at least one actuation element for a decoupling of the shoe adapter and the shoe connector from each other.

9. The wearable sitting-posture assisting device according to claim 8, wherein in an actuation the actuation element displaces the latch element relative to a magnet element at least indirectly.

10. The wearable sitting-posture assisting device according to claim 8, wherein the actuation element can be actuated at least substantially parallel to the at least one longitudinal leg axis.

11. A method for an operation of a wearable sitting-posture assisting device according to claim 1, wherein in at least one method step the shoe adapter and the shoe connector are coupled with each other at least transversely to the at least one longitudinal leg axis of the leg unit, wherein the quick coupling couples the shoe adapter and the shoe connector with each other without a tool, wherein the at least one latch element of the quick coupling at least partially realizes the coupling of the shoe adapter with the shoe connector.

* * * * *